(12) United States Patent
Demers et al.

(10) Patent No.: US 9,848,761 B2
(45) Date of Patent: Dec. 26, 2017

(54) METHOD AND APPARATUS FOR FIBERSCOPE EMPLOYING SINGLE FIBER BUNDLE FOR CO-PROPAGATION OF IMAGE AND ILLUMINATION

(71) Applicant: Research & Development International Inc., Pasadena, CA (US)

(72) Inventors: Joseph R. Demers, Pasadena, CA (US); Marek Sekowski, Pacific Palisades, CA (US)

(73) Assignee: Research & Development International, Inc., Pasadena, CA (US)

( * ) Notice: Subject to any disclaimer, the term of this patent is extended or adjusted under 35 U.S.C. 154(b) by 426 days.

(21) Appl. No.: 14/209,794

(22) Filed: Mar. 13, 2014

(65) Prior Publication Data

US 2014/0336465 A1    Nov. 13, 2014

Related U.S. Application Data

(60) Provisional application No. 61/786,510, filed on Mar. 15, 2013.

(51) Int. Cl.
*A61B 1/07* (2006.01)
*A61B 1/00* (2006.01)
(Continued)

(52) U.S. Cl.
CPC .............. *A61B 1/07* (2013.01); *A61B 1/002* (2013.01); *A61B 1/00096* (2013.01); *A61B 1/00163* (2013.01); *A61B 1/00165* (2013.01); *A61B 1/00167* (2013.01); *A61B 1/00188* (2013.01); *A61B 1/042* (2013.01); *A61B 1/06* (2013.01);
(Continued)

(58) Field of Classification Search
CPC ....... A61B 1/0607; A61B 1/07; A61B 1/0661; A61B 1/0669; A61B 1/0684; A61B 1/00117; A61B 1/00126; A61B 1/00163; A61B 1/00165; A61B 1/00167; A61B 1/0017; A61B 1/00174; A61B 1/00177; A61B 1/00179; A61B 1/00181; A61B 1/00183; A61B 1/00186; A61B 1/00188; A61B 1/0019; A61B 1/00193; A61B 1/02; A61B 1/042; A61B 1/055; A61B 1/06; A61B 1/0615; A61B 1/0623; A61B 1/063;
(Continued)

(56) References Cited

U.S. PATENT DOCUMENTS

2002/0026100 A1    2/2002  Ouchi
2006/0158896 A1*   7/2006  Krupa ..................... A61B 1/07
                                                                362/555

(Continued)

OTHER PUBLICATIONS

The International Search Report and the Written Opinion of the International Searching Authority for International Application No. PCT/US2014/029818 which is associated with U.S. Appl. No. 14/209,794, dated Jul. 4, 2014, Korean Intellectual Property Office, Republic of Korea.

(Continued)

*Primary Examiner* — Ryan Henderson
(74) *Attorney, Agent, or Firm* — Pritzkau Patent Group, LLC

(57) ABSTRACT

An exemplary embodiment providing one or more improvements includes an endoscope which utilizes a single coherent fiber bundle for simultaneously carrying imaging and illumination light.

15 Claims, 18 Drawing Sheets

(51) Int. Cl.
*A61B 1/002* (2006.01)
*A61B 1/06* (2006.01)
*A61B 1/04* (2006.01)

(52) U.S. Cl.
CPC .......... *A61B 1/0607* (2013.01); *A61B 1/0661* (2013.01); *A61B 1/0669* (2013.01); *A61B 1/0676* (2013.01)

(58) Field of Classification Search
CPC ... A61B 1/0638; A61B 1/0646; A61B 1/0653; A61B 1/0676
See application file for complete search history.

(56) References Cited

U.S. PATENT DOCUMENTS

| | | |
|---|---|---|
| 2008/0007733 A1 | 1/2008 | Marks et al. |
| 2008/0058600 A1 | 3/2008 | Bowman |
| 2008/0269563 A1* | 10/2008 | Takahashi ............ A61B 1/0653 600/178 |
| 2009/0257723 A1 | 10/2009 | Namati et al. |
| 2011/0134656 A1 | 6/2011 | Kitano |

OTHER PUBLICATIONS

International Preliminary Report on Patentability for International Application No. PCT/US2014/029818 which is associated with U.S. Appl. No. 14/209,794, dated Mar. 12, 2015, Korean Intellectual Property Office, Republic of Korea.

\* cited by examiner

METHOD AND APPARATUS FOR FIBERSCOPE EMPLOYING SINGLE FIBER BUNDLE FOR CO-PROPAGATION OF IMAGE AND ILLUMINATION

RELATED APPLICATIONS

The present application claims priority from U.S. Provisional Application Ser. No. 61/786,510, filed on Mar. 15, 2013, which is hereby incorporated by reference.

BACKGROUND

Because of their utility and versatility, fiberscopes are employed in extremely diverse applications: from nuclear reactor inspection to medical diagnosis. The ability to image an object that would normally be impossible to access without extremely invasive methods is indispensable in many fields.

In general terms, a fiberscope employs a flexible bundle of glass fibers to transmit an image from the distal end of the fibers, which can be positioned adjacent to the object to be imaged, to the proximal end of the fibers which can be positioned in a more accessible location. The bundle of fibers used for imaging can be referred to as an imaging fiber bundle. Current technology makes it possible to construct a sub-mm diameter imaging fiber that incorporates thousands of individual fibers. For instance, an imaging fiber bundle having 10,000 individual fibers that each have a 5 um diameter can have an outer diameter of only 0.5 mm. During imaging, each fiber serves as a pixel for the image and transmits this pixel via internal reflection from the distal end of the fiber to the proximal end of the fiber. The individual fiber size determines the pixel size for the transmitted image, and the size and density of the fibers influence the bending flexibility of the imaging fiber bundle.

Since the distal ends of the fibers in the imaging fiber bundle cannot image the object, fiberscopes require a distal imaging lens to image the object onto the surfaces of the distal ends of the fibers. The surfaces of the distal ends of the fibers can also be referred to as the distal end face of the imaging fiber bundle. In addition, since the proximal end of the imaging fiber bundle is very small, a viewing device is used to magnify the image that has been transmitted along the image fiber to the proximal end of the imaging fiber bundle so that the image can be viewed. The viewing device can utilize a lens arrangement and/or electronic sensor to magnify the image for viewing.

Effective utilization of the fiberscope generally requires illumination because fiberscopes are commonly employed to interrogate cavities which have little or no light. In conventional fiberscopes, this illumination is commonly provided by a series of physically distinct fibers that are dispersed around the circumference of the image fiber and are connected to a light source. In contrast to the imaging fiber, these illumination fibers are generally fewer in number and much larger in diameter than the imaging fibers. These illumination fibers are physically distinct from one another and from the imaging fibers. Further, the illumination fibers are separated from the imaging fibers using an opaque material such as a plastic jacket and, typically, the illumination fibers can each include a cladding and/or jacket.

Some fiberscopes can also be used for performing tasks at the distal end of the scope. These fiberscopes can include an integral tool that is incorporated into the distal end of the scope for performing a specific task. Other types of such fiberscopes can include one or more working channels into which different types of tools can be inserted and guided to the distal end of the scope for performing a variety of different tasks. Fiberscopes having one or more working channels can provide more flexibility for performing tasks as compared to fiberscopes with integrated tools.

A common challenge in fiberscope construction and, in particular, medical endoscopes, is seen with respect to economical construction and utilization. For instance, a medical endoscope having features as described could cost thousands of dollars. Disposal of such a device after a single use is prohibitively expensive. Therefore, the used endoscope is typically returned to the manufacturer for sterilization. Such a service, particularly for what is considered a bio-hazard, can be expensive. Accordingly, it is desirable to decrease the cost of a fiberscope while maintaining the quality and versatility of the device.

The foregoing examples of the related art and limitations related therewith are intended to be illustrative and not exclusive. Other limitations of the related art will become apparent to those of skill in the art upon reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In general, a method and associated apparatus are described for a fiberscope employing a single fiber bundle for co-propagating image and illumination light. In an embodiment, an endoscope is disclosed having an elongated coherent fiber bundle that includes a distal end and a proximal end. The coherent fiber bundle includes a plurality of different fibers that are surrounded by a common cladding and the coherent fiber bundle is configured to transfer light between the distal and proximal ends through the fibers. A working assembly includes an elongated probe having a distal end for insertion into a viewing area and a proximal end for manipulating the distal end of the probe. The distal end of the elongated coherent fiber bundle is positioned at the distal end of the probe. An imaging assembly includes a viewing device for receiving and modifying image light for viewing. The proximal end of the coherent fiber bundle can be positioned at the imaging assembly and the imaging assembly can be configured to transfer image light from the proximal end of the coherent fiber bundle to the viewing device. An illumination light source, forming part of the imaging assembly, can generate illumination light and insert the illumination light into the proximal end of the coherent fiber bundle which transfers the illumination light to the distal end of the coherent fiber bundle. The illumination light source is arranged such that the illumination light is inserted into the proximal end of the coherent fiber bundle at least essentially without the illumination light interacting with the image light between the proximal end of the coherent fiber bundle and the viewing device. A lens arrangement can form part of the working assembly and can be positioned at the distal end of the elongated probe, the lens arrangement includes an illumination portion arranged to receive illumination light from the distal end of the coherent fiber bundle and to disperse the illumination light into the viewing area. The lens arrangement also includes an imaging portion that is different than the illumination portion and that is arranged to receive image light from the viewing area including illumination light reflected from the viewing area and to insert the image light into the distal end of the coherent fiber bundle for transfer to the proximal end of the coherent fiber bundle where the image light is then transferred to the imaging assembly.

In another embodiment, an endoscope working assembly is disclosed which includes an elongated coherent fiber bundle having a distal end and a proximal end. The coherent fiber bundle includes a plurality of different fibers that are surrounded by a common cladding and the coherent fiber bundle is configured to transfer light between the distal and proximal ends using the fibers. An elongated probe has a distal end for insertion into a viewing area and a proximal end for manipulating the distal end of the probe. The distal end of the elongated coherent fiber bundle is positioned at the distal end of the probe. A lens arrangement can be positioned at the distal end of the elongated probe, the lens arrangement can include an illumination portion arranged to receive illumination light emitted from the distal end of the coherent fiber bundle and to disperse the illumination light into the viewing area. The lens arrangement can also include an imaging portion that is different than the illumination portion and that is arranged to receive image light from the viewing area that includes illumination light reflected from the viewing area and to insert the image light into the distal end of the coherent fiber bundle for transfer of the image light to the proximal end of the coherent fiber bundle. The coherent fiber bundle simultaneously emits the illumination light and receives the image light. A working assembly connector portion of an optical connector can be included for selectively optically coupling the working assembly to an imaging assembly having an imaging assembly connector portion of the optical connector. The working assembly connector portion can be connected to the proximal end of the coherent fiber bundle and is arranged to simultaneously transfer image light to the imaging assembly through coherent fiber bundle and receive illumination light from the imaging assembly through the coherent fiber bundle.

In another embodiment, an endoscope is disclosed which includes an elongated coherent fiber bundle having a distal end and a proximal end. The coherent fiber bundle includes a plurality of different fibers that are surrounded by a common cladding and the coherent fiber bundle is configured to transfer light between the distal and proximal ends using the fibers. A working assembly is included having an elongated probe with a distal end for insertion into a viewing area and a proximal end for manipulating the distal end of the probe. The distal end of the elongated coherent fiber bundle is positioned at the distal end of the probe. The working assembly can also include a lens arrangement positioned at the distal end of the probe and configured for transferring image light from the viewing area into the distal end of the coherent fiber bundle which carries the image light to the proximal end of the coherent fiber bundle and for transferring illumination light from distal end of the coherent fiber bundle into the viewing area. An imaging assembly can be included having a viewing device for receiving and modifying the image light for viewing. The proximal end of the coherent fiber bundle can be positioned at the imaging assembly and the imaging assembly can include an objective lens that is configured to transfer the image light from the proximal end of the coherent fiber bundle to the viewing device. An illumination light source arrangement can be included, which can form part of the imaging assembly, for inserting illumination light into the proximal end of the coherent fiber bundle which transfers the illumination light to the distal end of coherent fiber bundle. The coherent fiber bundle simultaneously carries the illumination light and the image light using the same fibers in the fiber bundle. The illumination light source arrangement produces polarized illumination light in a first orientation. A polarizing beam splitter, forming part of the imaging assembly, can be included and can be arranged to receive the first orientation polarized illumination light from the illumination light source arrangement. The polarizing beam splitter can reflect the first orientation polarized illumination light into the proximal end of the coherent fiber bundle for transfer by the coherent fiber bundle to the distal end of the coherent fiber bundle to illuminate the viewing area. The coherent fiber bundle and the viewing area randomize the polarization of the first orientation polarized light and the coherent fiber bundle also randomizes the polarization of the image light, which includes illumination light that is reflected by the viewing area. The polarizing beam splitter can also be configured to reflect polarized light having the first orientation received from the proximal end of the coherent fiber bundle, toward the illumination light source arrangement. The polarizing beam splitter can be arranged in a path of the image light between the proximal end of the coherent fiber bundle and the imaging assembly objective lens. The polarizing beam splitter can be configured to pass image light, that includes a second polarized orientation that is different than the first polarized orientation, to the imaging assembly objective lens for transfer to the viewing device.

In another embodiment, a method and associated apparatus are described for endoscopically imaging a viewing area in a cavity. A distal end of an endoscope probe can be inserted into the cavity. The endoscope probe can include a coherent fiber bundle having a plurality of different fibers that are surrounded by a common cladding and the coherent fiber bundle is configured to transfer light between a distal end and a proximal end through the fibers. The coherent fiber bundle can be arranged with the distal end of the coherent fiber bundle at the distal end of the probe. And the illumination light can be inserted into the proximal end of the coherent fiber bundle which transfers the illumination light from the proximal end of the coherent fiber bundle to the distal end of the coherent fiber bundle. The illumination light can be dispersed from the distal end of the coherent fiber bundle into the viewing area of the cavity. The image light can be received from the viewing area and inserting the image light into the distal end of the coherent fiber bundle which transfers the image light from the distal end of the coherent fiber bundle to the proximal end of the coherent fiber bundle. The image light can include illumination light reflected from the viewing area. The coherent fiber bundle simultaneously transfers the illumination light and the image light. The image light can be guided from the proximal end of the coherent fiber bundle to a viewing device and the image light and the viewing device can be used to display an image of the viewing area.

In addition to the exemplary aspects and embodiments described above, further aspects and embodiments will become apparent by reference to the drawings and by study of the following descriptions.

DETAILED DESCRIPTION

The following description is presented to enable one of ordinary skill in the art to make and use the invention and is provided in the context of a patent application and its requirements. Various modifications to the described embodiments will be readily apparent to those skilled in the art and the generic principles taught herein may be applied to other embodiments. Thus, the present invention is not intended to be limited to the embodiments shown, but is to be accorded the widest scope consistent with the principles and features described herein including modifications and equivalents, as defined within the scope of the appended claims. It is noted that the drawings are not to scale and are diagrammatic in nature in a way that is thought to best illustrate features of interest. Descriptive terminology may be adopted for purposes of enhancing the reader's understanding, with respect to the various views provided in the Figures, and is in no way intended as being limiting.

Figure 1:
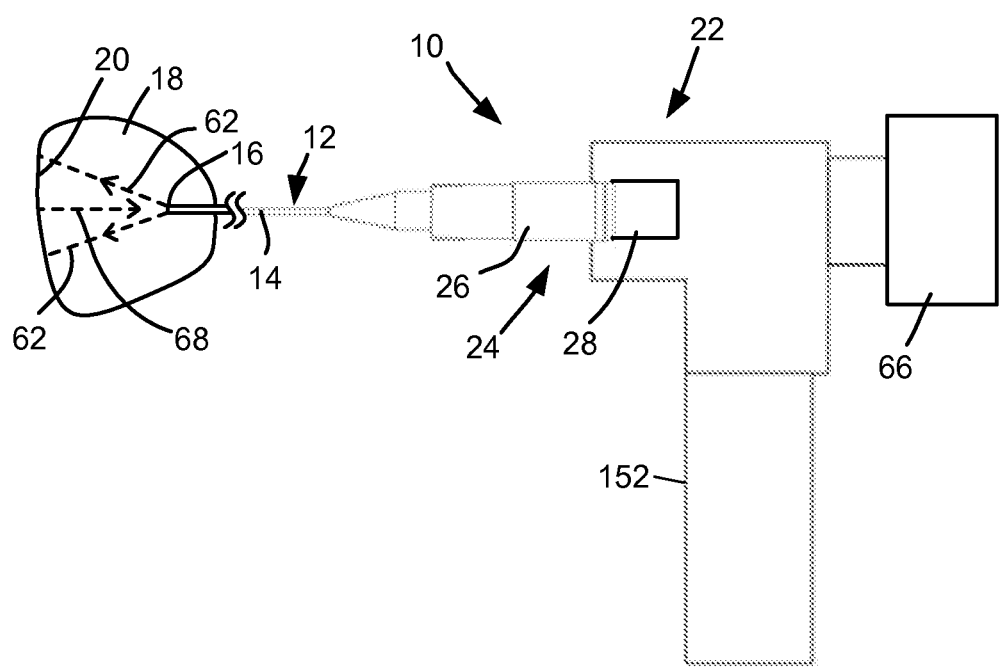
FIG. 1 is a diagrammatic view, in elevation, of an embodiment of an endoscope which utilizes a single coherent fiber bundle for simultaneously transferring illumination light and imaging light.

Attention is now directed to the Figures wherein like reference numbers may refer to like components throughout the various views. FIG. 1 is a representation of an endoscope, corresponding to an embodiment of the present disclosure, and generally indicated by the reference number 10. The endoscope includes a working assembly 12 which has an elongated probe 14 with a distal end 16 that can be used for inserting into a cavity 18 for illuminating and imaging a viewing area 20. The endoscope also includes an imaging assembly 22 for receiving images from the working assembly and for modifying the images so that they can be viewed. The endoscope can include a connector 24 so that working assemblies, such as working assembly 12, can be selectively connected and disconnected to the imaging assembly. This allows for the disposal of the working assemblies after the working assemblies have been used and the reuse of the imaging assembly. Connector 24 can include a working assembly connector portion 26 and an imaging assembly connector portion 28 which have complementary configurations to allow them to engage one another. The connector is arranged to optically couple the working assembly and the imaging assembly.

Figure 2:
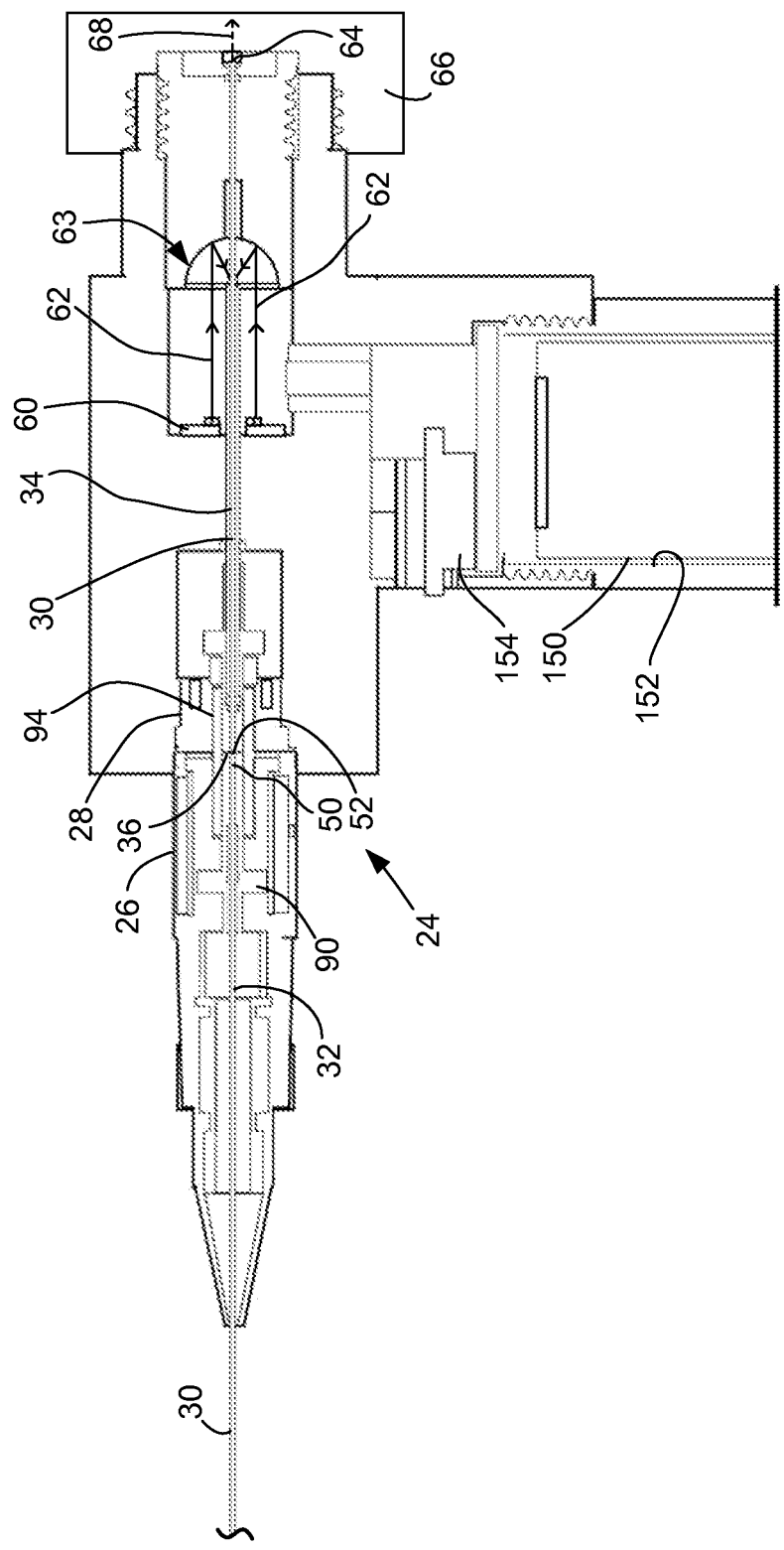
FIG. 2 is an enlarged diagrammatic partially cut-away view of a portion of the endoscope shown in FIG. 1.

Referring now to FIG. 2, endoscope 10 also includes a single coherent fiber bundle arrangement 30 which extends from distal end 16 of the probe of the working assembly to the imaging assembly. As shown in the present embodiment, coherent fiber bundle arrangement 30 includes a first bundle or segment 32 that is part of the working assembly and a second bundle or segment 34 that is part of the imaging assembly. Segments 32 and 34 are optically coupled to one another using connector 24 at an optical interface 36.

Figure 3:
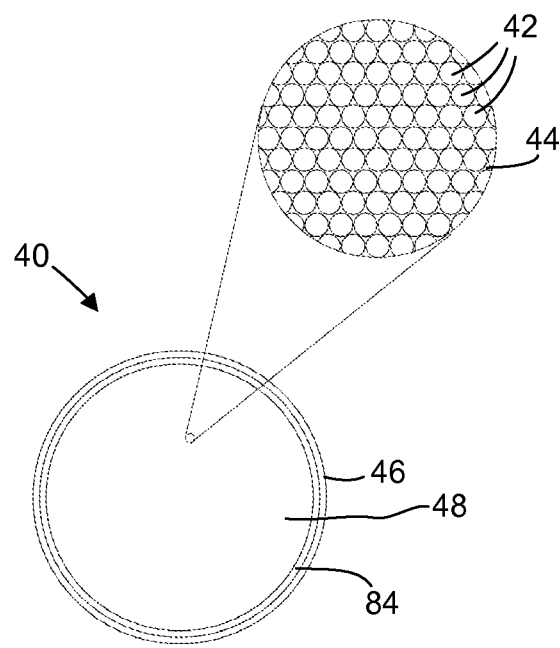
FIG. 3 is a diagrammatic illustration of an imaging fiber end.
Figure 4:
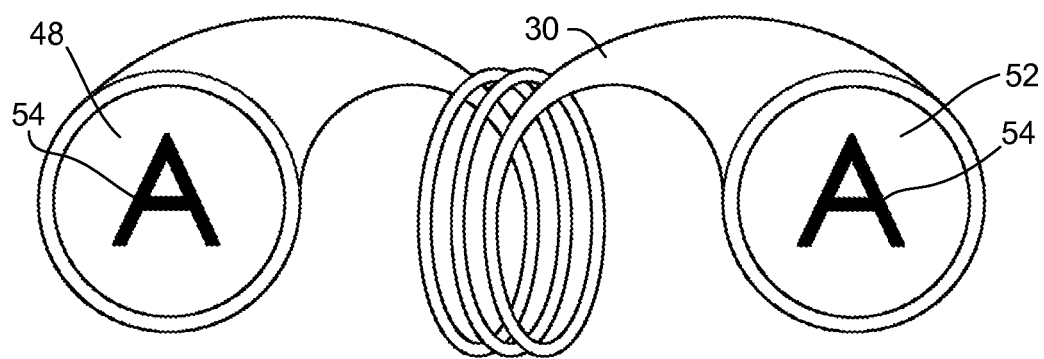
FIG. 4 is a diagrammatic illustration of a spatially consistent imaging fiber.

Referring now to FIG. 3, a diagrammatic illustration is shown of a distal end 40 of coherent fiber bundle arrangement 30. In the present embodiment, distal end 40 is located at distal end 16 of the probe (FIG. 1). The coherent fiber bundle includes multiple individual fiber cores 42 that are surrounded individually and collectively by a common cladding 44 (shown in an inset view). The fiber cores and cladding are surrounded by a jacket 46 which can have more than one layer. The distal end faces of the individual fiber cores can be collectively referred to as a distal end face 48 of the fiber bundle and it is through these end faces of the individual fiber cores that light enters and exits the coherent fiber bundle. Working assembly segment 32 has a proximal end 50 (FIG. 2) with a proximal end face 52 at optical interface 36. As diagrammatically shown in FIG. 4, fiber bundle arrangement 30 is referred to as coherent because the fiber core ends at distal end face 48 are spatially consistent with the fiber core ends at the proximal end face 52 so that an image, such as image 54, is carried through the fiber bundle without being changed by the arrangement of the fiber cores.

Referring again to FIG. 2, in the present embodiment, endoscope 10 includes a light source 60 that is located in imaging assembly 22 for generating an illumination light 62. An optical arrangement 63 receives the light from the source and inserts the illumination light into a proximal end 52 of coherent fiber bundle arrangement 30 at optical interface 36. Illumination light 62 is carried through the coherent fiber bundle arrangement to the distal end face of the fiber bundle where the illumination light is guided to the viewing area (FIG. 1). Endoscope 10 also includes a viewing device 66 for receiving image light 68 from proximal end 64 and modifying the image light for viewing. Image light 68 includes illumination light that is reflected from viewing area 20 and that is guided into the distal end face of the coherent fiber bundle arrangement and is carried by the fiber bundle arrangement to the proximal end of the fiber bundle at the imaging assembly. The single coherent fiber bundle arrangement simultaneously carries the illumination light and the imaging light between the working assembly and imaging assembly. As disclosed herein, at any given location along the single fiber bundle arrangement, a single coherent fiber bundle simultaneously carries both the illumination and imaging light. That is, no more than one fiber bundle is present at any location, without the need for two or more fiber bundles extending parallel to one another, for example, with imaging light carried by one fiber bundle and illumination light carried by one or more other bundles.

Figure 5:
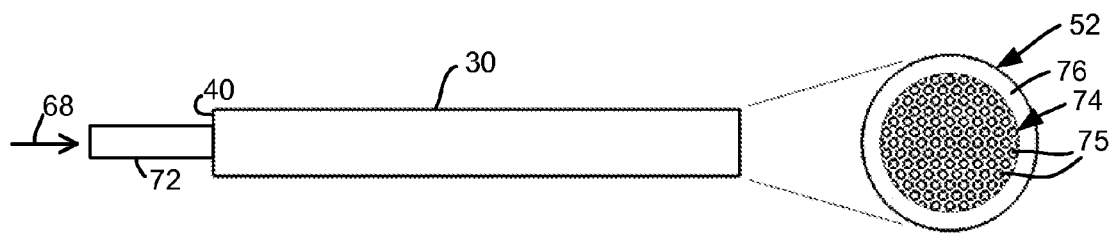
FIG. 5 is a diagrammatic illustration of a coherent fiber bundle and lens which can be used with the endoscope shown in FIG. 1.

Referring now to FIG. 5, an embodiment is shown in which a single coherent fiber bundle arrangement, such as fiber bundle arrangement 30, can be employed for both imaging and illumination. In this embodiment, an imaging lens, such as a gradient-index (GRIN) lens 72, with a smaller diameter than distal end face 40 is positioned at the distal end of the fiber bundle arrangement to image the viewing area in order to guide the image light into an imaging portion 74 of the fiber cores of the bundle, as shown by highlighting the imaging portion of the fiber cores at proximal end face 52 (FIG. 2) which, of course, is spatially consistent with distal end 40. In this embodiment, imaging portion 74 is a circular area at least approximately in the center of the distal end face which leaves fiber cores 75 arranged circumferentially around imaging portion 74 to define an annular area end face 76 which can be utilized for carrying illumination light 62. By utilizing a single coherent fiber bundle arrangement for both illumination and imaging, the total number of components of the working assembly of the endoscope is reduced along with the cost to produce the working assembly. Reducing the cost of the working assembly provides for economic feasibility with respect to a disposable embodiment. Accordingly, for purposes of the present disclosure and the appended claims, a coherent fiber bundle can be considered to encompass a single coherent fiber bundle as well as an arrangement of multiple fiber bundle segments that are optically coupled end-to-end.

Figure 6:
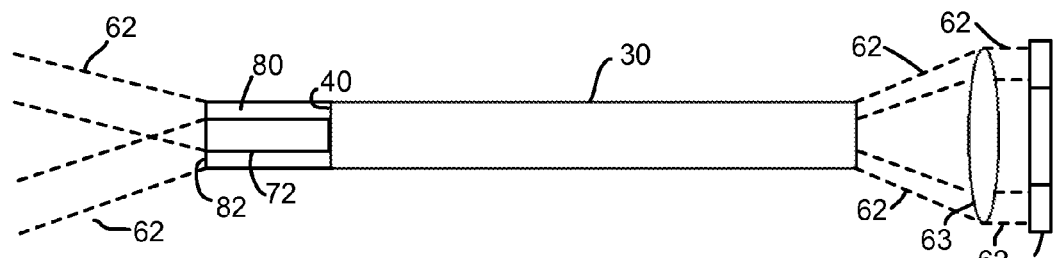
FIG. 6 is a diagrammatic illustration of the illumination light entering and exiting the coherent fiber bundle along with optics at each end of a fiber bundle arrangement.
Figure 7:
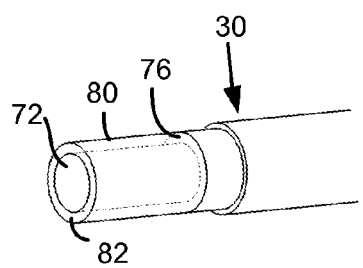
FIG. 7 is an enlarged diagrammatic illustration, in perspective, of a distal end of a coherent fiber bundle and an embodiment of associated optics in accordance with the present disclosure.

Referring now to FIGS. 6 and 7 in conjunction with FIG. 5, a cylinder 80 is positioned at the distal end of the imaging fiber bundle arrangement in order to effectively deliver illumination light from the distal end to the viewing area. Cylinder 80 can be glass or any suitable material such as, for example, plastic which can guide light from the end faces of the fiber cores in annular area 76 to the viewing area. For purposes of convenience, such a cylinder may be referred to as a glass cylinder, however, such references are not intended as being limiting. In an embodiment, the cylinder can contain a fluorescing phosphor to convert narrowband illumination, such as blue illumination from an LED, to white light. Since LED light is inherently narrowband, using fluorescing phosphor in the cylinder can convert the narrowband light from the LED into a white light which can be much more suitable for illuminating a viewing area. Cylinder 80 can include an end face 82 which can have a texture, such as frosted, to disperse the illumination light into the viewing area to promote an even illumination field. Applicants recognize that the end face can also be rounded to produce a highly divergent lens which can also have the effect of dispersing the illumination. As is discussed in more detail, illumination light 62 from light source 60 is guided into the annular area using optical arrangement 63. Because the outer dimension of glass cylinder 80 can be essentially the same diameter as that of the imaging fiber and the inner dimension can be essentially the same diameter as the GRIN lens, the GRIN lens can be passively placed in the cylinder and relative to the distal end face of the imaging fiber bundle for imaging. That is, such passive placement does not involve the need for an optical alignment procedure which can be complex and time-consuming. The GRIN lens can be passively placed in the glass cylinder at the end of the fiber cores by sliding the lens into the glass cylinder, for example, using an interference or pressed fit between the lens and the cylinder to assure centricity and proper alignment with the fiber bundle. Passive placement of the GRIN lens can decrease the manufacturing costs of the working assembly.

Figure 8:
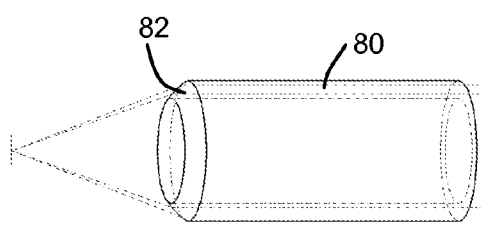
FIG. 8 is an enlarged diagrammatic illustration of an embodiment of a cylindrical lens that can be used at the distal end of the coherent fiber bundle as part of the optics of FIG. 7.

Referring now to FIG. 8 in conjunction with FIGS. 6 and 7, in an embodiment the end face of cylinder 80 can be polished so that the illumination light is concentrated to an area at a specific distance from the end face of the cylinder and the imaging lens. In an embodiment, the polished cylinder end face can also be used to deliver laser radiation, either continuously or pulsed. In this embodiment, the laser radiation replaces the illumination light. The ability to focus optical radiation is dependent upon the wavelength of the radiation and the aperture of the focusing optics. For instance and in general, the larger the optic employed for focusing, the tighter the focus which can be achieved (several assumptions are made for illustrative purposes). In this regard, a focus spot size can be dependent upon the diameter of the cylinder even though only an external annular ring is being illuminated by the laser. In this case, the end of the glass cylinder can be polished to produce a focus at a specific point in front of the imaging optic. An appropriate optical flux through the cylinder can be provided with light from the associated optical fiber bundle.

Figure 9:
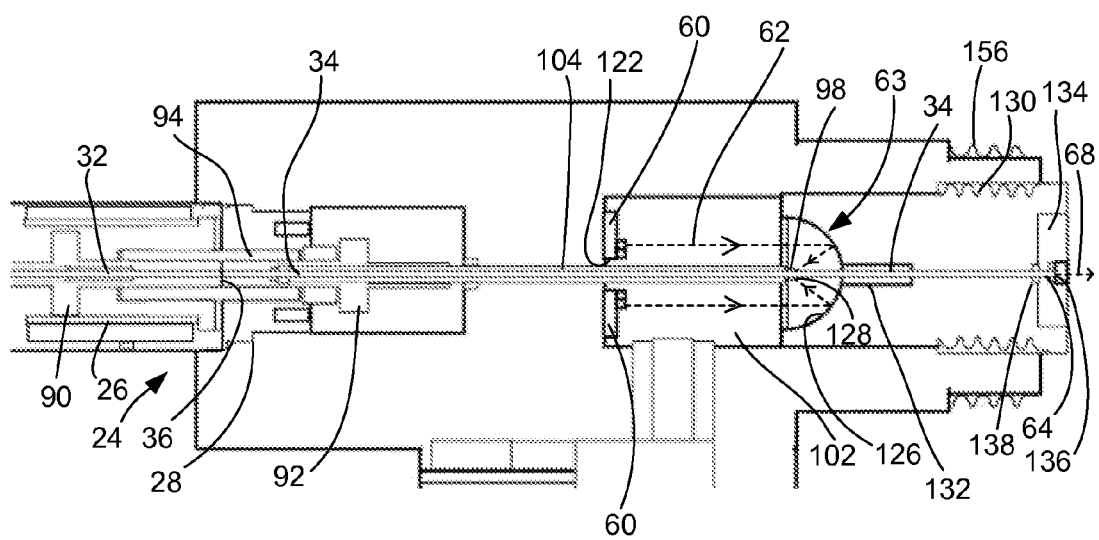
FIG. 9 is an enlarged partially cut-away view, in elevation, of a portion of the endoscope shown in FIG. 1.

Referring now to FIG. 9 in conjunction with FIG. 2, an embodiment of a working assembly connector portion 26 includes a ferrule 90 and imaging assembly connector portion 28 includes a ferrule 92. Working assembly connector portion 26 includes a working assembly ferrule 90 and imaging assembly connector portion 28 includes an imaging assembly ferrule 92. Connector 24 also includes a connector mating sleeve 94 for axially aligning the working assembly and imaging assembly ferrules. The connector mating sleeve can be part of either the working assembly or imaging assembly connector portion. Working assembly ferrule 90 is installed on working assembly segment 32 and imaging assembly ferrule 92 is installed on imaging assembly segment 34 of the coherent fiber bundle. The ends of the fiber cores of the segments can be polished and are coplanar with the ends of the ferrules. When the working assembly connector portion and imaging assembly connector portion are mated to one another, as shown in FIGS. 2 and 9, imaging and illumination light can be transferred between the working assembly and imaging assembly across optical interface 36. The connector can also include a latching mechanism to secure the connection. In an embodiment, the connector can utilize standard optical fiber connectors such as, for example SC and SMA type connectors.

In order to illuminate the viewing area using illumination light carried by circumferentially arranged fiber cores 75 (FIG. 5), it is necessary to illuminate the proximal end of the coherent fiber bundle in a manner which only illuminates the circumferential fibers at least essentially without the illumination light interacting with the image light between the proximal end of the fiber bundle and the viewing device. Thus, at least to an approximation, the illumination light is not coupled to the fibers carrying imaging light or reflected to the viewing assembly at the proximal end to a detectable or noticeable degree, at least from a practical standpoint or in terms of normal human vision perception. Furthermore, the illumination must be within the numerical aperture (NA) of the fibers so that the illumination is coupled into a supported mode of the fiber to avoid bleeding of the illumination light into the imaging fibers during propagation. Applicants bring to light herein several embodiments for achieving the desired results.

Figure 10A:
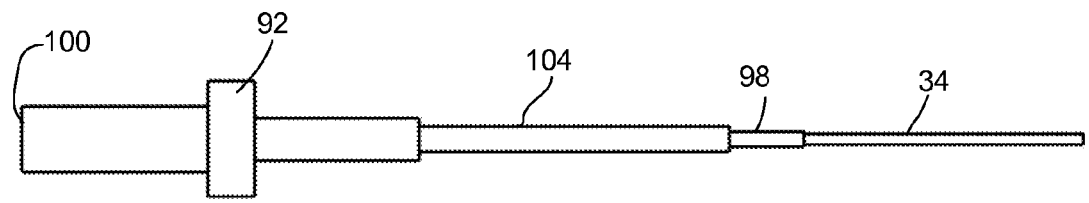
FIGS. 10a and 10b are diagrammatic illustrations of certain light guiding components of the endoscope shown in FIG. 1 in elevational and partially cut-away views, respectively.
Figure 10B:
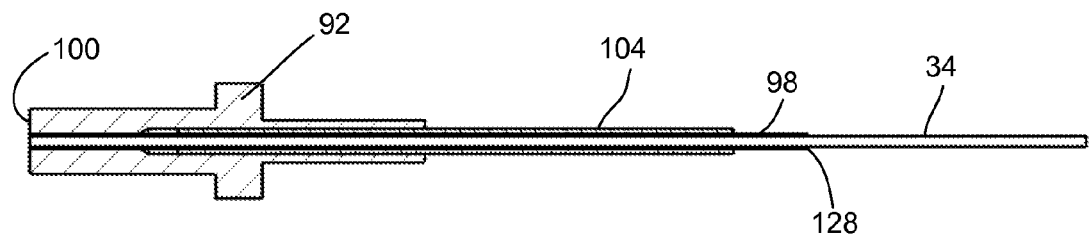

Referring now to FIGS. 10a and 10b in conjunction with FIG. 9, FIG. 10a is a diagrammatic view in elevation of an arrangement of light guiding components in an elevational view while FIG. 10b illustrates the components in a partially cut-away elevational view. Optical arrangement 63 can include a light guiding cylinder, such as a glass cylinder 98 that is supported by imaging assembly connector portion 28 and arranged to have a distal end face that is coplanar with a distal end face 100 of imaging assembly ferrule 92 and a proximal end that extends into an imaging assembly illumination cavity 102. The glass cylinder can be similar to the one described previously that is mounted on the distal end of the probe except that cylinder 98 is longer. The cylinder can concentrically support a center imaging fiber such as, for example, imaging assembly segment 34. A support tube 104, which can be formed, for example, from stainless steel, can be incorporated to protect the glass cylinder. With proper tolerances, the construction can be assembled readily and concentrically; for example, the imaging assembly segment, cylinder and support tube can be glued to the imaging assembly ferrule.

Figure 11A:
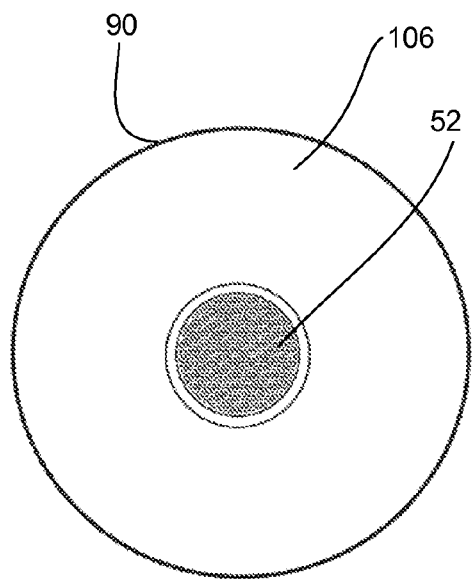
FIGS. 11a and 11b are diagrammatic illustrations of end faces, in elevation, of embodiments of components of a connector, coherent fiber bundles, and a light guiding component of the endoscope shown in FIG. 1.
Figure 11B:
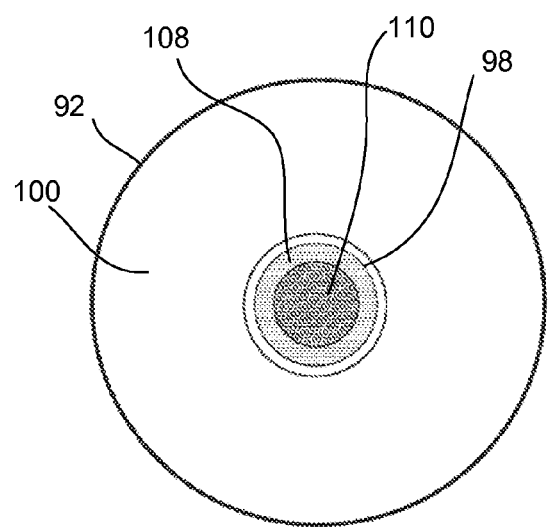

Referring now to FIGS. 11a and 11b in conjunction with FIG. 9, FIGS. 11a and 11b diagrammatically illustrate end faces, in elevation, of various components in relation to terminating a fiber bundle assembly. A proximal end face 106 is shown of working assembly ferrule 90 which includes proximal end face 52 of working assembly segment 32. FIG. 11b illustrates distal end face 100 of imaging assembly ferrule 92 which includes a distal end face 108 of glass cylinder 98 and a distal end face 110 of imaging assembly segment 34 of the coherent fiber bundle. In one embodiment, the cross-sectional diameter of the bundle of fibers at proximal end face 52 of working assembly segment 32 is 500 µm; the outside diameter of glass cylinder 98 is 500 µm, the inside diameter of glass cylinder 98 is 360 µm; and the cross-sectional diameter of the image light carrying fibers at distal end face 110 is 350 µm. In this arrangement, when illumination light is passed from the imaging assembly to the working assembly across optical interface 36, proximal end face 52 receives the illumination light from end face 108 of glass cylinder 98 into the fiber cores arranged in the annular area represented by fiber cores 75 in FIG. 5. On the other hand, when image light is passed from the working assembly to the imaging assembly across optical interface 36, the image light passes from image light carrying fiber cores 74 (FIG. 5) into distal end face 110 of the imaging assembly segment of the coherent fiber bundle. It should be understood that either a GRIN lens or rod can receive and carry the image light from imaging portion 74 of the fiber cores when used in place of the imaging assembly segment of the coherent fiber bundle arrangement.

Figure 12:
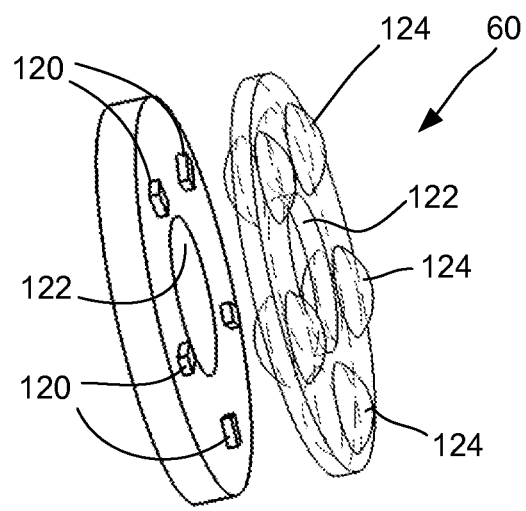
FIG. 12 is a diagrammatic illustration, in perspective, of an embodiment of a light source which can be used with the endoscope shown in FIG. 1.

Referring now to FIG. 12 in conjunction with FIG. 9, an embodiment of illumination light source 60 is an annularly shaped arrangement having a series of light producing elements such as, for example, light emitting diodes (LEDs) 120 for producing illumination light 62 (FIG. 2). The illumination light source can include a circuit board upon which the light producing elements are mounted. These light producing elements can be lasers, ultraviolet radiation sources and other kinds of sources of radiation in addition to or in place of the LEDs. The LEDs are arranged around an aperture 122 and the light source includes lenslets 124, which can be formed in a piece of plastic and which are arranged to collimate the light from the LEDs. The illumination light source receives power from a power source such as, one or more batteries 150 that can be located in a battery tube 152 (FIG. 2). The light source is connected to the power source through a power control assembly 154 which can include a dimmer control thumbwheel for controlling the lumen output of the light source.

Referring to FIG. 9, light source 60 can be positioned in illumination cavity 102 such that glass cylinder 98 and imaging assembly segment 34 of the coherent fiber bundle extend through aperture 122 and across the cavity. Optical arrangement 63 can include a parabolic mirror 126 can be positioned at an opposite end of the illumination cavity from the light source. The parabolic minor can be concentrically arranged around a center axis that is common with glass cylinder 98 and can be a focusing mirror that receives light and focuses the light into an annular area. By way of example, the parabolic mirror can be machined from metal. The illumination light is generated and collimated into a ring shape by the light source such that the ring of light strikes the parabolic mirror and is reflected from the parabolic mirror into the glass cylinder through a proximal end face 128 of the glass cylinder. The glass cylinder then carries the illumination light using internal reflectance to the working assembly segment of the coherent fiber bundle arrangement which carries the illumination light to the distal end of the working assembly probe.

The parabolic mirror can be supported in the illumination cavity via threads 130 which can be used to move the parabolic minor closer or further from the light source can modify the location to which light is reflected relative to the proximal end face of the glass cylinder. The imaging assembly segment of the coherent fiber bundle arrangement extends through a bore 132 in the parabolic mirror to an imaging cavity 134 where a proximal end face 136 of the imaging assembly segment is positioned. A multi-pitch GRIN rod lens can be used in place of imaging assembly segment 34 to transmit image light from optical interface 36 to imaging cavity 134. The imaging assembly segment can be centered in bore 132 using an O-ring 138. The glass cylinder can terminate short of the end of the imaging fiber which it encases and can be slightly longer than the protective stainless steel sheath. Imaging assembly segment 34 can be coated on the outside with paint or metallization to effectively prevent illumination light from entering the imaging fiber. An O-ring (not shown) can be positioned around the imaging assembly segment of the coherent fiber bundle where the segment passes through the parabolic minor. This O-ring can center the fiber in the parabolic mirror without allowing the fiber to contact the surface of the minor and can block illumination light from escaping from the illumination cavity into imaging cavity 134 where the illumination light could interfere with the imaging light.

Figure 13:
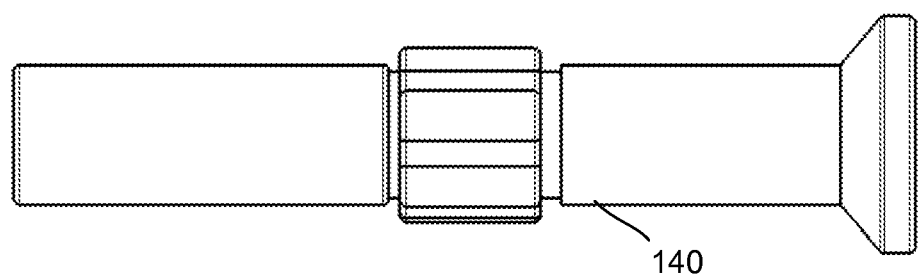
FIG. 13 is a diagrammatic illustration, in elevation, of an embodiment of an eyepiece viewing device.

Viewing device 66 (FIG. 1) can be an eyepiece 140 (FIG. 13) or an electronic viewing device such as an array of light sensors and an electronic display. The viewing device (see item 66 of FIG. 2) can be supported and positioned relative to the proximal end face of coherent fiber bundle 136 (FIG. 9), for example, using threads 156 in order to receive the image light from the fiber (or GRIN rod lens) and to enlarge and/or otherwise modify the image light such that the images can be viewed. Eyepiece 140 can include an arrangement of lenses which can be adjusted to image the proximal end of the fiber bundle and to enlarge the image for viewing. These threads can also be employed to connect a viewing device in the form of a microscope objective and a camera.

Figure 14:
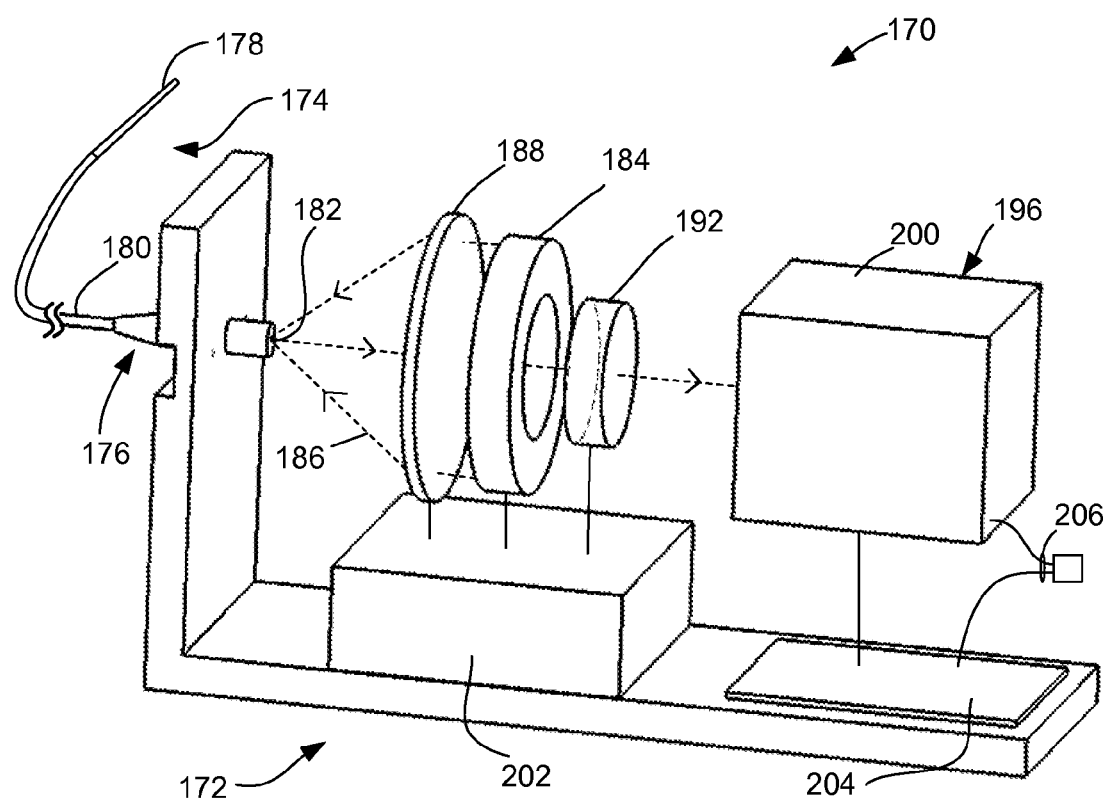
FIG. 14 is a diagrammatic view, in perspective, of another embodiment of an endoscope in accordance with the present disclosure and shown here to illustrate details of its structure.
Figure 15:
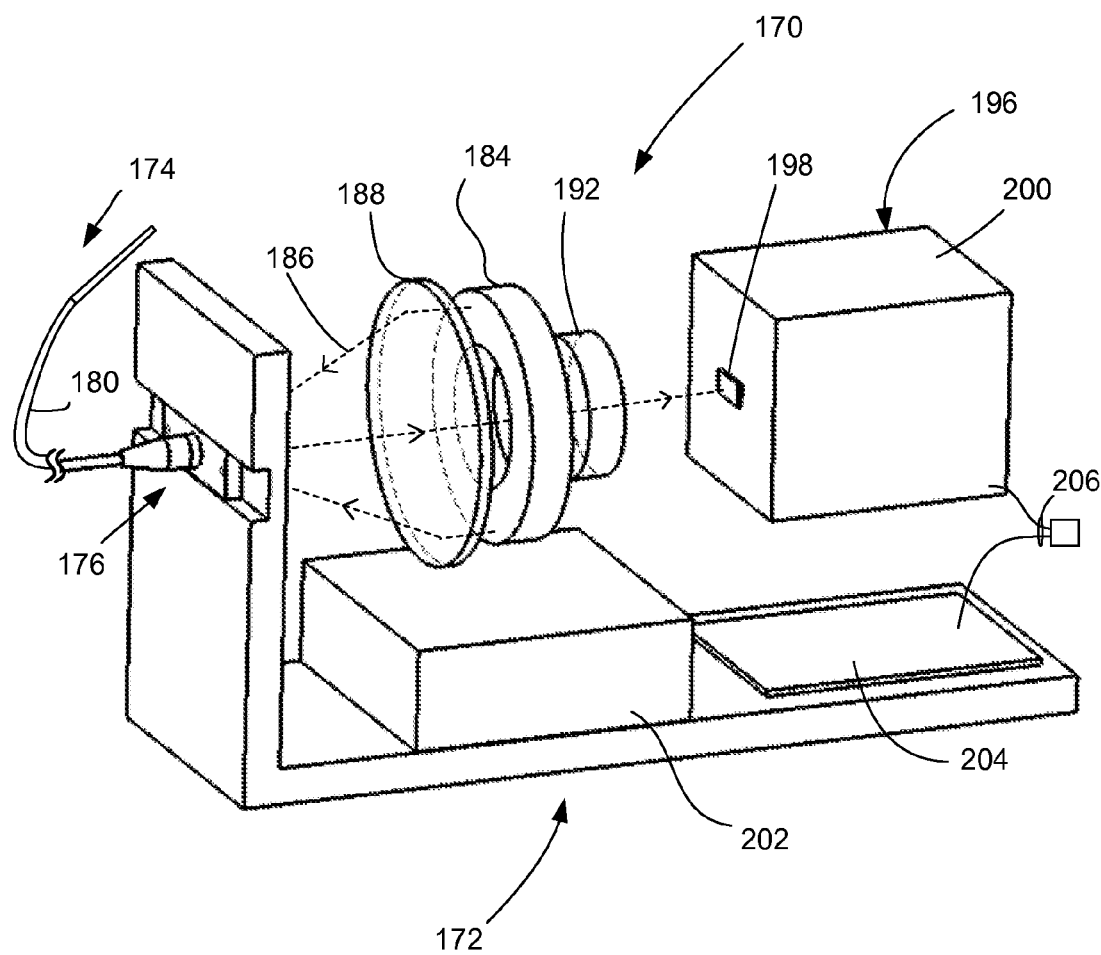
FIG. 15 is another diagrammatic view, in perspective, of the endoscope shown in FIG. 14 shown here to illustrate further details of its structure.

Referring now to FIGS. 14 and 15, an endoscope 170 is shown in opposing perspective views. The present embodiment can utilize a single coherent fiber bundle for simultaneously carrying illumination light and imaging light in an endoscope. Endoscope 170 includes an imaging assembly 172 and a working assembly 174 which can be optically coupled to one another using a connector 176. Working assembly 174 includes a probe 178 for inserting into a viewing area. The probe can include a cylinder and objective lens such as those shown in FIGS. 6 and 7 for illuminating and imaging the viewing area, respectively. The working assembly includes a coherent fiber bundle 180 that has a proximal end face 182 (seen in FIGS. 14, 16 and 17) that is positioned in the imaging assembly when the working assembly is mated to the imaging assembly using the connector. Although the proximal end face of the coherent fiber bundle is diagrammatically illustrated in FIGS. 16 and 17 such that individual fiber cores 183 along with a common cladding 185 can be easily seen, in practice the coherent fiber bundle can have thousands of individual fiber cores. In one embodiment, the coherent fiber bundle can have tens of thousands of fiber cores and can have an outside diameter of approximately 1 mm. The proximal end face of the coherent fiber bundle can be polished to define a common plane that is perpendicular to a center axis of the fiber bundle.

Imaging assembly 172 includes a light source 184 that is arranged in a ring, or annular shape to produce an illumination light 186 in an annular shape. The imaging assembly can also include an illumination lens 188 that images the illumination light from the light source, as examples, onto annular areas 190a (FIG. 16) and 190b (FIG. 17) of the proximal end face of the coherent fiber bundle. Imaging assembly 172 also includes an imaging lens 192 which images center areas 194a (FIG. 16) and 194b (FIG. 17) that are inside of the respective annular areas onto a viewing device 196. In the embodiment shown in FIGS. 14 and 15 the viewing device includes a CCD array 198 and a camera 200.

Figure 16:
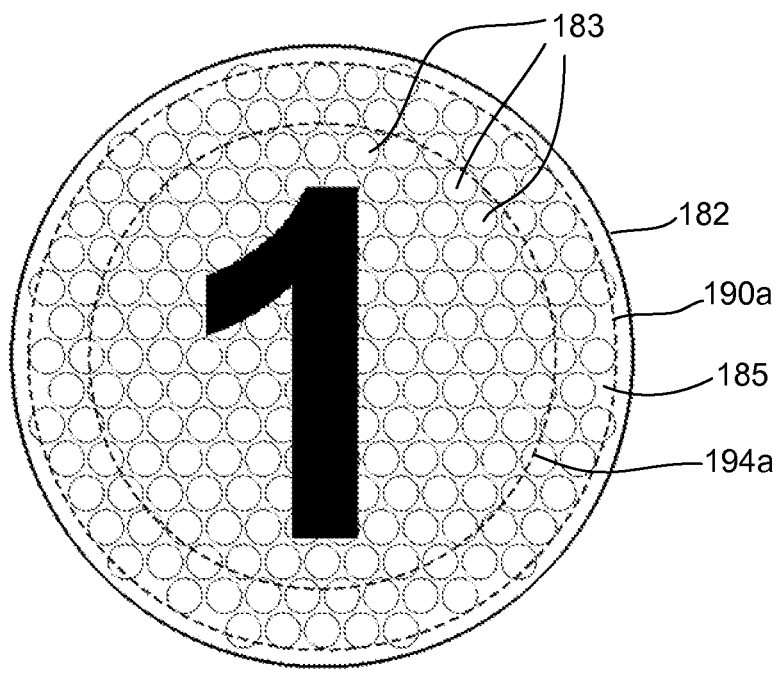
FIG. 16 is a diagrammatic view, in elevation, of an end face of a coherent fiber bundle showing imaging and illumination areas.
Figure 17:
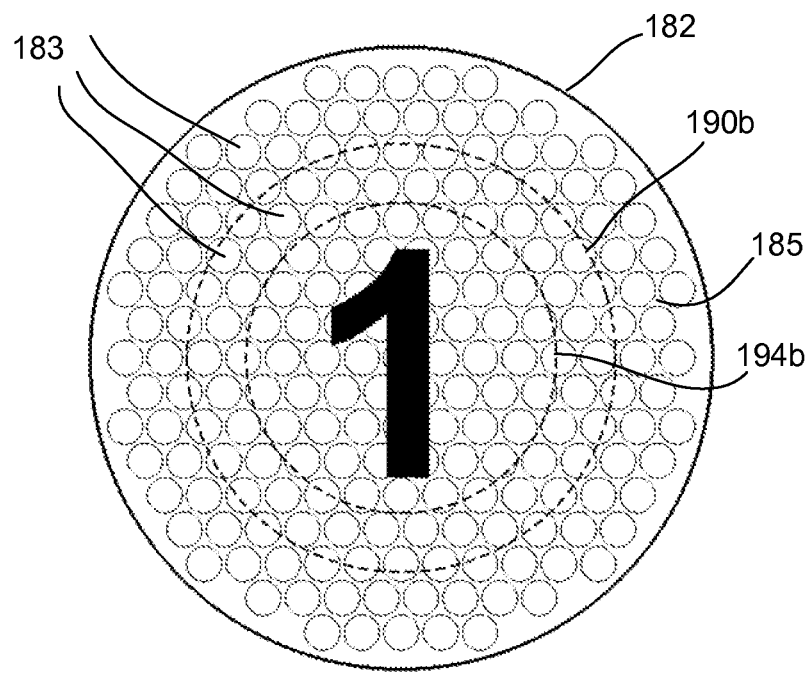
FIG. 17 is a diagrammatic illustration, in elevation, of the end face of the coherent fiber bundle shown in FIG. 16 shown here to illustrate embodiments of imaging and illumination areas.

By utilizing appropriate optics, imaging assembly 172 can adapt to connect and operate with disposable working assemblies having coherent fiber bundles with various diameters. For instance, if a disposable working assembly employing a coherent bundle with 50,000 individual fibers and a diameter of 1.1 mm is connected to the imaging assembly, the optics (such as the illumination and imaging lenses) and/or the light source and viewing device, can be adjusted such that the outer circumference of the illumination light (annular area 190) is at the maximum radius of the end face and the image that is transmitted by the endoscope is maximized, as shown in FIG. 16. However, if a disposable working assembly with a smaller imaging fiber is attached to the imaging assembly, the imaging and illumination optics and/or the position of the light source and viewing device can be adjusted to produce the situation shown in FIG. 17 where the annular area of the illumination light and the image are correspondingly smaller. The relatively smaller annular and imaging areas are shown in FIG. 17 on the end face of the relatively larger fiber bundle to illustrate the reduction in size of these areas. In an instance where a relatively smaller imaging fiber bundle is used, the relatively smaller annular and imaging areas shown in FIG. 17 can be sized such that the entire end face of the smaller imaging fiber bundle is utilized. Adjusting the optics and/or other components can be accomplished using one or more mechanical stages, such as mechanical stage 202 which can be motorized and can be controlled using a circuit 204. One or more electrical cables such as electrical cable 206 can be connected to the viewing device and/or stage control circuit. The electrical cable can be used for transmitting image data from the imaging device and power to the imaging device. Suitable electrical cabling can also be used for sending and receiving signals to control and power the mechanical stages. For example, electrical cabling can include a standard USB or other configuration.

It should be appreciated that combining the image and the illumination/radiation into the same fiber allows a single fiber optic connector to be employed for coupling disposable working assemblies to the imaging assembly since a single connector can transfer both illumination and imaging light between the working assembly and the imaging assembly. Standard off-the-shelf components can be employed to make this connection. For example, a standard fiber optic connector can have an internal ceramic or metal ferrule with an I.D. of anywhere from 230 um to 1580 um. Standard imaging fiber diameters (with coating stripped away) vary from 210 um to 1500 um and can be inserted into and for connection to a corresponding fiber optic connector. The connector can include one or more ferrules, which can be ceramic or metal components that form part of many fiber optic connectors. Standard fiber optic connectors are extremely economical in quantity.

Figure 18:
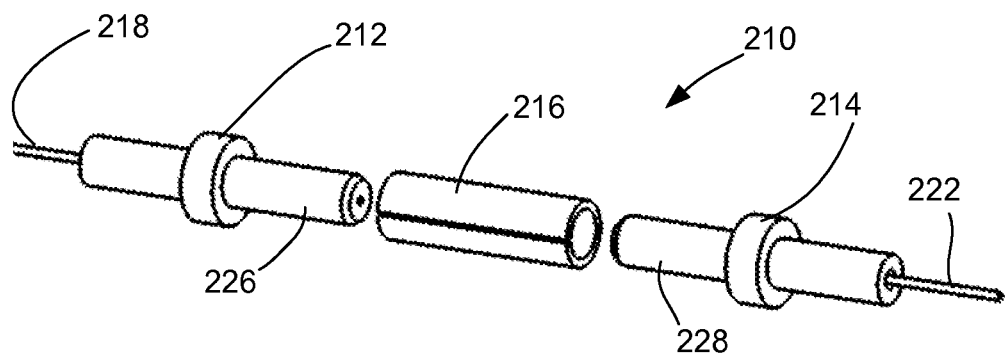
FIG. 18 is a diagrammatic illustration, in perspective, of components of an embodiment of an optical connector for use as part of an endoscope for simultaneously transferring imaging and illumination light in accordance with the present disclosure.
Figure 19:
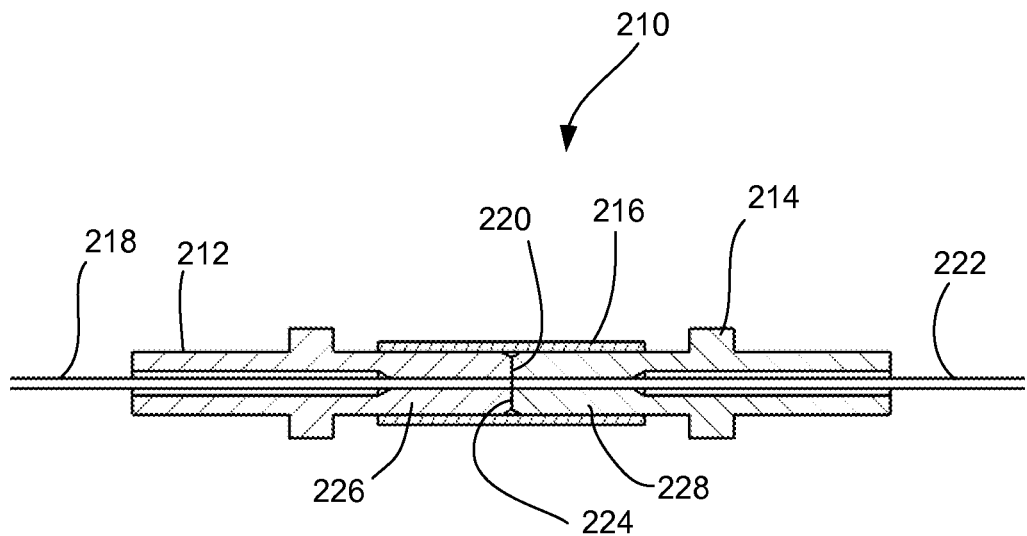
FIG. 19 is a diagrammatic, partially cut-away illustration of an embodiment of components of an optical connector in a connected mode for use in an endoscope to simultaneously transfer imaging and illumination light in accordance with the present disclosure.

Referring now to FIGS. 18 and 19, an optical connector 210 is shown in a perspective view and a partially cut-away view, respectively, for simultaneously transferring illumination and imaging light between a working assembly and an imaging assembly of an endoscope. The connector is shown in a simplified version in that it does not show components such as a latching mechanism. Although connector 210 is not shown in relation to the remainder of the working and imaging assemblies, it should be understood that such optical connectors can be at least partially integrated into the working assembly and/or the imaging assembly or can be positioned between other components of the working and imaging assemblies. Connector 210 includes a working assembly ferrule 212 and an imaging assembly ferrule 214 along with a connector mating sleeve 216. The working assembly ferrule is attached to a working assembly fiber segment 218 having a proximal end face that is polished and is coplanar with a working assembly ferrule end face 220 (FIG. 19). Imaging assembly ferrule 214 is attached to an imaging assembly fiber segment 222 that has a distal end face that is polished and is coplanar with an imaging assembly ferrule end face 224. These end faces can be highly polished so that the surfaces are relatively flat and free of pits and scratches. Ferrule 212 includes a barrel 226 and ferrule 214 includes a barrel 228. The portion of fiber segment 218 in barrel 226 is coaxial with barrel 226 and the portion of the fiber segment 222 in barrel 228 is coaxial with barrel 228. The ferrule end faces have an extremely tight tolerance of perpendicularity to the center axis of their respective barrels. When the connector optically couples the working assembly and the imaging assembly, end face 220 abuts end face 224 and the proximal end of working assembly fiber segment 218 is axially aligned with the distal end of imaging assembly fiber segment 222 by axially aligning barrel 226 with barrel 228 using connector mating sleeve 216.

Figure 20:
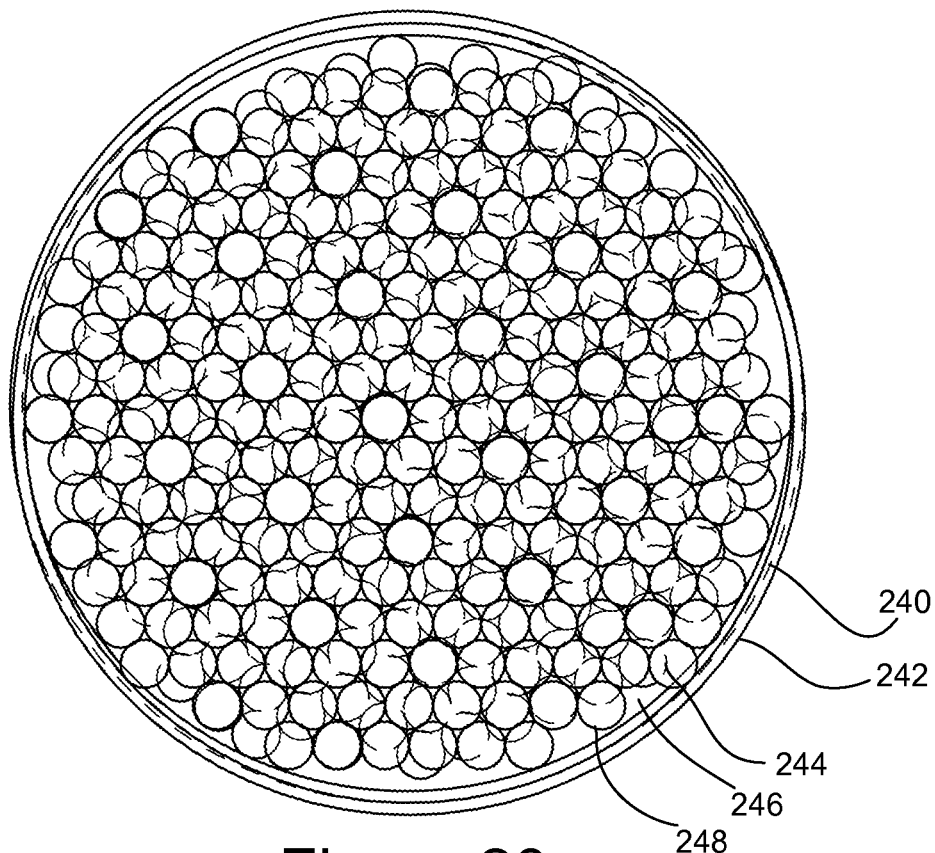
FIG. 20 is a diagrammatic illustration, in elevation, of misaligned ends of two coherent fiber bundles.
Figure 21:
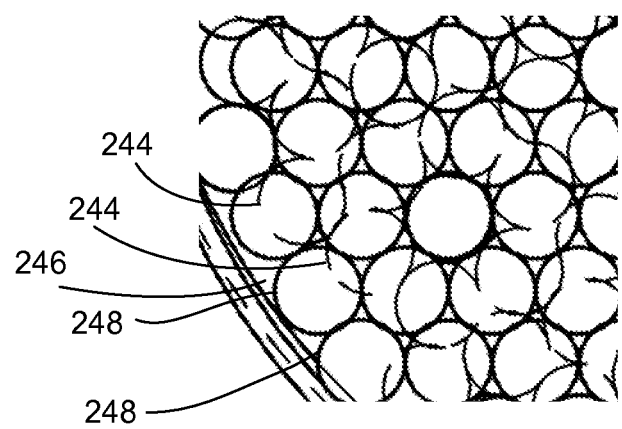
FIG. 21 is a diagrammatic, further enlarged, fragmentary view of a portion of FIG. 20, shown here to illustrate further details with respect to the relationship between the fiber core ends of the coherent fiber bundles.

Referring now to FIGS. 20 and 21, a proximal end face 240 of a working assembly fiber segment is shown relative to a distal end face 242 of an imaging assembly fiber segment. The imaging assembly fiber segment includes fiber cores 244 and cladding 246 and the working assembly fiber segment includes fiber ends 248. As FIGS. 20 and 21 diagrammatically illustrate, even if the imaging assembly and working assembly fiber segments include the same number of fiber cores and those fiber cores are similarly spatially oriented, lateral and/or rotational misalignment of the fibers can cause one of fiber ends 248 of the working assembly to partially optically couple into three fiber ends 244 and cladding 246 of the imaging assembly fiber segment. This can have the effect of decreasing the pixel number and can cause the image passed between the fibers to be blurred. Even if the fiber ends of one working assembly fiber segment were aligned with the fiber ends of an imaging assembly fiber segment, it is extremely unlikely that alignment could be achieved for a different working assembly fiber segment that is part of another disposable working assembly. Discontinuities caused by this situation can be removed, for example, using software. In an embodiment, the working assembly can be shipped with a tip protector (cap) over the distal tip of the probe having a calibration image on a surface of the cap that confronts the distal tip. The working assembly can be calibrated before the tip protector is removed.

Figure 22:
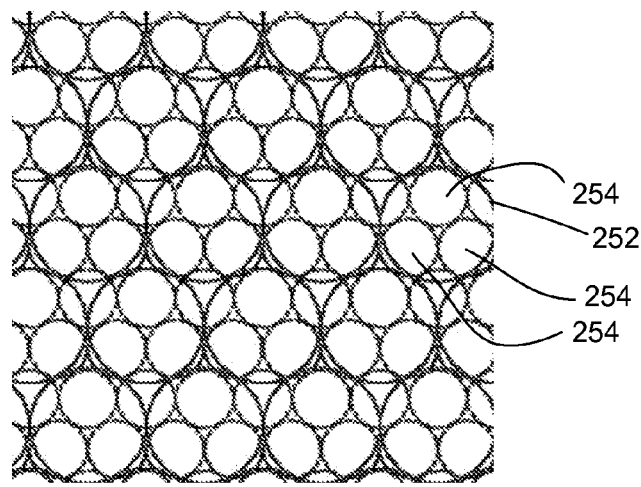
FIG. 22 is a diagrammatic, fragmentary illustration of a relationship between the fiber core ends of two coherent fiber bundles having different fiber core densities.

Referring now to FIG. 22 in conjunction with FIGS. 18 and 19, another approach to remove errors in the image due to axial and/or rotational misalignment in the interface involves selecting imaging assembly fiber segment 222 having a higher fiber density than working assembly fiber segment 218. In this arrangement, each fiber core 252 of working assembly fiber segment 218 with optically couples to multiple fiber cores 254 of imaging assembly fiber segment 222 to therefore increase the pixel number at the imaging assembly relative to the working assembly. Since the imaging assembly is reused with different disposable working assemblies any increase in the cost resulting from the use of the higher density fiber is a one-time cost per endoscope that can easily be absorbed.

Figure 23:
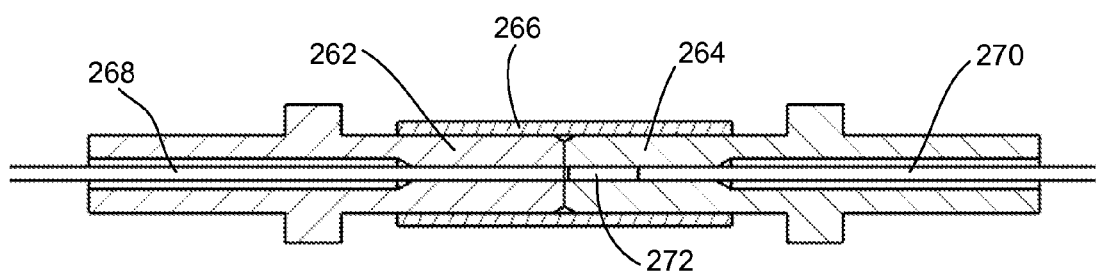
FIG. 23 is a diagrammatic, partially cut-away illustration of components of another embodiment of an optical connector for use in an endoscope for simultaneously transferring imaging and illumination light.

Referring now to FIG. 23, a connector 260 is shown in an elevational, partially cut-away view for simultaneously transferring illumination and imaging light between a working assembly and an imaging assembly of an endoscope. Connector 260 includes a working assembly ferrule 262, an imaging assembly ferrule 264 and a connector mating sleeve 266. A working assembly fiber segment 268 is attached to ferrule 262 and an imaging assembly fiber segment 270 is attached to ferrule 264. Connector mating sleeve 266 axially aligns ferrules 262 and 264 to axially alignment working assembly fiber segment 268 and imaging assembly fiber segment 270. Connector 260 also includes a GRIN lens 272 which, in the embodiment shown in FIG. 23, is positioned in ferrule 264. Lens 272 can be a single pitch GRIN or similar lens that is arranged to image between the proximal end face of working assembly fiber segment 268 and the distal end face of the imaging assembly fiber segment. The lens in connector 260 is operable even in the presence of a gap between the proximal end face of the working assembly fiber segment and the lens.

Figure 24:
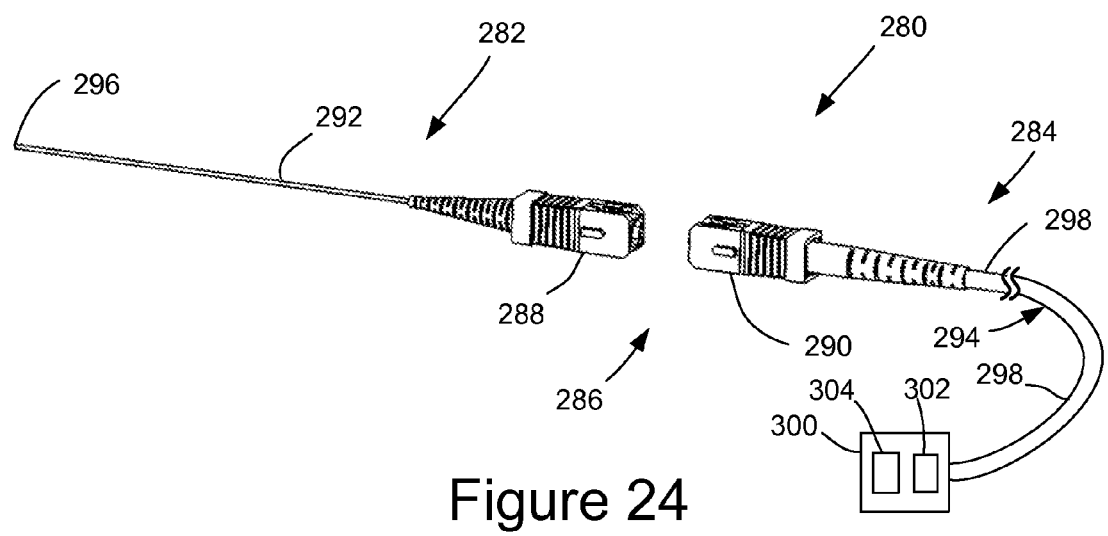
FIG. 24 is a diagrammatic illustration, in partial perspective, of an embodiment of an endoscope including a connector integrated as part of the working assembly.

Referring now to FIG. 24, another embodiment of an endoscope is shown in a partial perspective view, generally indicated by the reference number 280. While a connector in a previous embodiment is shown with the imaging assembly connector portion integrated into the imaging assembly the connector can be positioned in other locations. For example, endoscope 280 includes a working assembly 282 and imaging assembly 284 which can selectively be coupled to one another using a connector 286. Connector 286 includes a working assembly connector portion 288 and an imaging assembly connector portion 290. In this embodiment, the working assembly connector portion is integrated into the working assembly which includes a probe 292 that contains a working assembly segment (not shown) of a coherent fiber bundle arrangement 294 and components (not shown) for imaging and for dispersion of illumination light at a distal end 296. The imaging assembly connector portion supports a distal end of an imaging assembly segment 298 of coherent fiber bundle arrangement 294. The imaging assembly segment extends from the imaging assembly connector portion to an imaging assembly body 300 which contains an illumination light source 302 for supplying illumination light to the distal end of the probe and an imaging assembly 304 for receiving imaging light from the distal end of the probe and for modifying the light for viewing.

Figure 25:
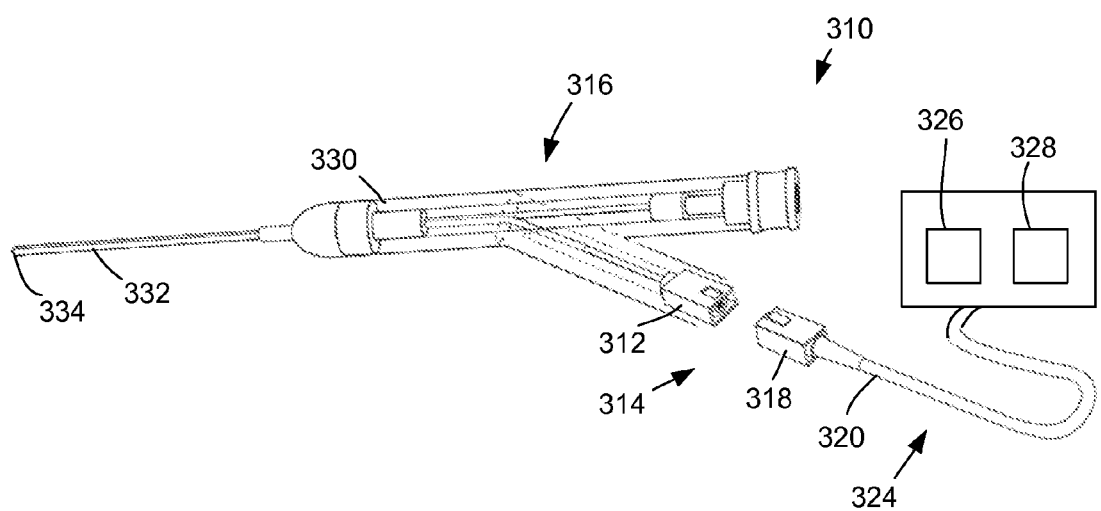
FIG. 25 is a diagrammatic illustration of an embodiment of an endoscope including a working assembly having a working channel in accordance with the present disclosure.
Figure 26:
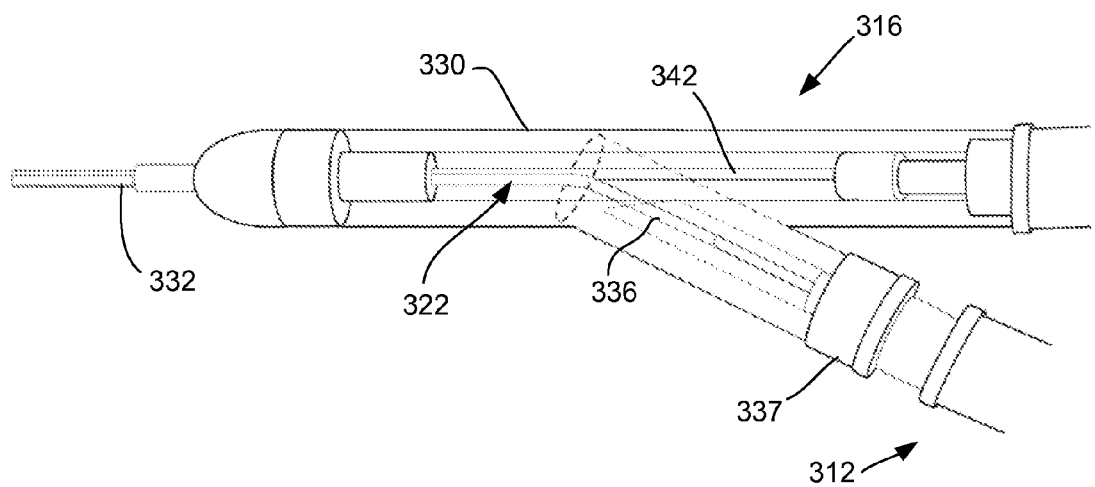
FIG. 26 is a diagrammatic view illustrating of a portion of the working assembly shown in FIG. 25.
Figure 27:
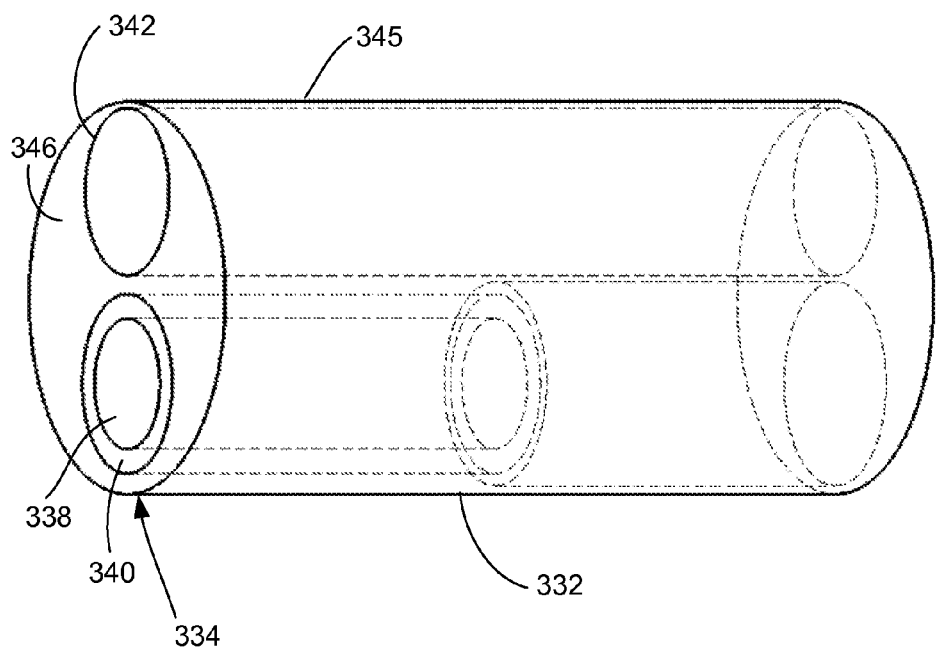
FIG. 27 is a diagrammatic illustration, in perspective, of an embodiment of a distal end of a probe of the working assembly shown in FIG. 25.

Referring now to FIGS. 25, 26 and 27, another embodiment of an endoscope, generally indicated by the reference number 310, is illustrated. Endoscope 310 includes a working assembly connector portion 312 of a connector 314 that is integrated into a working assembly 316. An imaging assembly connector portion 318 of connector 314 is attached to a distal end of an imaging assembly segment 320 of a coherent fiber bundle 322. A proximal end of the imaging assembly segment of the fiber bundle is connected to an imaging assembly body 324 which contains an illumination light source 326 and an imaging assembly 328. In the present embodiment, working assembly 316 includes a working assembly body 330 (which can be referred to as a Y-tube) and a probe 332 having a distal end 334. Although a single branch of a y-connector is shown, any number of additional branches or additional connectors may be utilized as practicable and/or desired to facilitate additional connections. Working assembly 316 includes a working assembly segment 336 (FIG. 26) of coherent fiber bundle 322 which extends between the working assembly connector portion of the connector and the distal end of the probe. FIG. 26 shows a custom metal adapter 337 which can be used for holding the ferrule of the working assembly connector portion of connector 314. An objective lens 338 and light guiding and dispersing cylinder 340 (FIG. 27) are positioned at the distal end of the working assembly fiber segment for imaging and illuminating a viewing area, respectively.

Endoscope 310 can be an exploratory tool which provides the ability to manipulate or sample material adjacent to the distal end of the probe. Working assembly 316 incorporates a working channel 342 through which tools, fluids, microwave probes, and the like can be passed from a proximal end 344 (FIG. 26) to a distal end 346 (FIG. 27). FIG. 27 illustrates a relationship between the working channel and the imaging optics at the distal end of the probe. Generally, the working channel and the imaging/illumination fiber can be held together by a probe sheath 345. While the desire of having an extremely economical endoscope does not preclude the use of fully integrated tools, the incorporation of a working channel can make endoscope 310 more economical than endoscopes with fully integrated tools.

Figure 28:
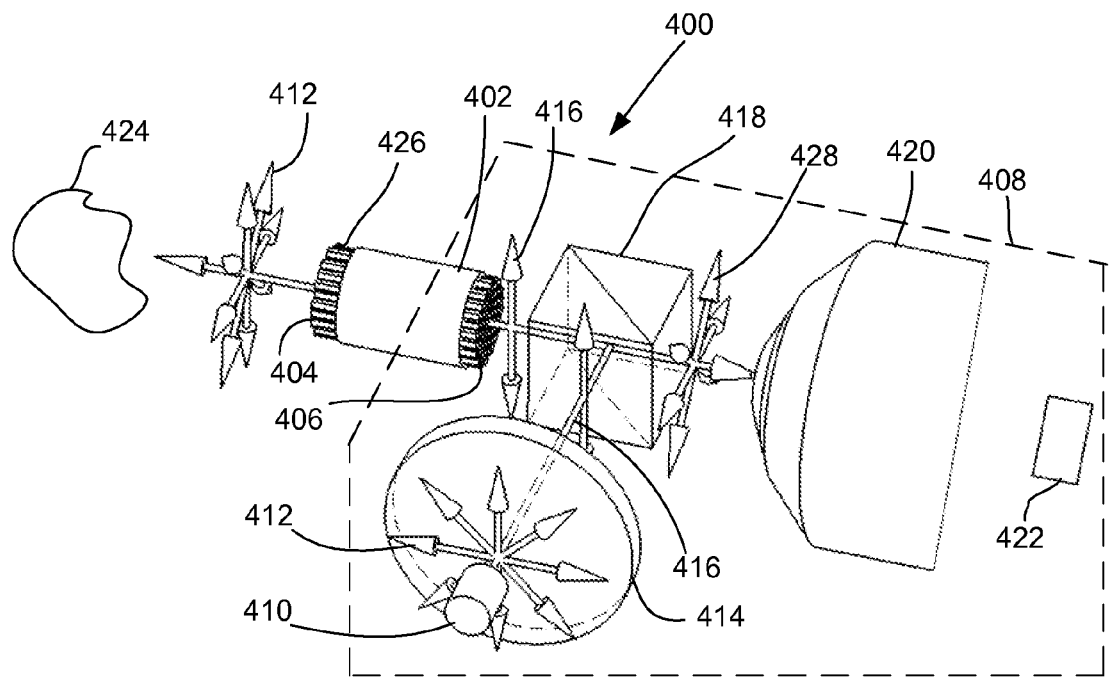
FIG. 28 is a diagrammatic illustration, in perspective, of an embodiment of an endoscope which utilizes a single coherent fiber bundle for simultaneously transferring illumination light and imaging light and which utilizes polarized light for illumination in accordance with the present disclosure.

Referring now to FIG. 28, an embodiment of an endoscope 400 is shown which uses a single coherent fiber bundle arrangement 402 for simultaneously carrying illumination and imaging light. In this embodiment, the imaging fiber along the entire length of the endoscope is employed to propagate the illumination and imaging light. Endoscope 400 utilizes polarization and rejection of reflected light. Fiber bundle 402 includes a distal end 404 and a proximal end 406. Distal end 404 can be positioned at a distal end of a working assembly probe (not shown) and proximal end 406 can be positioned at an imaging assembly 408. An optical connector (not shown) can be utilized for optically connecting the working assembly and imaging assembly. The imaging assembly includes a broad spectrum light source 410 to produce illumination light 412 which is collimated or focused and linearly polarized by a polarizer 414, for example, to produce an (S) polarized illumination light 416 which strikes a polarizing beam splitter 418. In the present embodiment, the polarizing beam splitter will reflect only (S) polarization and will allow (P) polarization and ratios of the two polarizations to pass through instead of being reflected. The (S) polarized light is therefore reflected by the beam splitter and impinges upon proximal end 406 of coherent fiber bundle 402. Reflections from this interface are specular in nature and therefore are not re-reflected by the beam splitter and pass back towards the light source instead of passing through an objective lens 420 and onto a camera CCD 422.

The cores of the fiber bundle, during propagation, will homogenize and randomize the linear polarization of the light originally introduced to the fiber bundle. This effect also takes place with respect to light collected for the camera. The illumination of the random geometry of an imaged object 424 by the imaging fiber and a lens 426 at the distal end of the fiber bundle further randomizes the polarization of collected image light 428. In addition, the (S) component in collected image light is caused mainly by high intensity specular highlights from the object. Such components maintain the original (S) state of polarization and are responsible for an extended intensity range of the collected light. The coaxial illumination and imaging system of endoscope 400 rejects the (S) component in the image light, making the image less dynamically challenging for the camera's automatic exposure settings. This can result in better exposure and higher image quality. It should be appreciated that, in another embodiment, the S and P polarizations can be interchanged.

Figure 29:
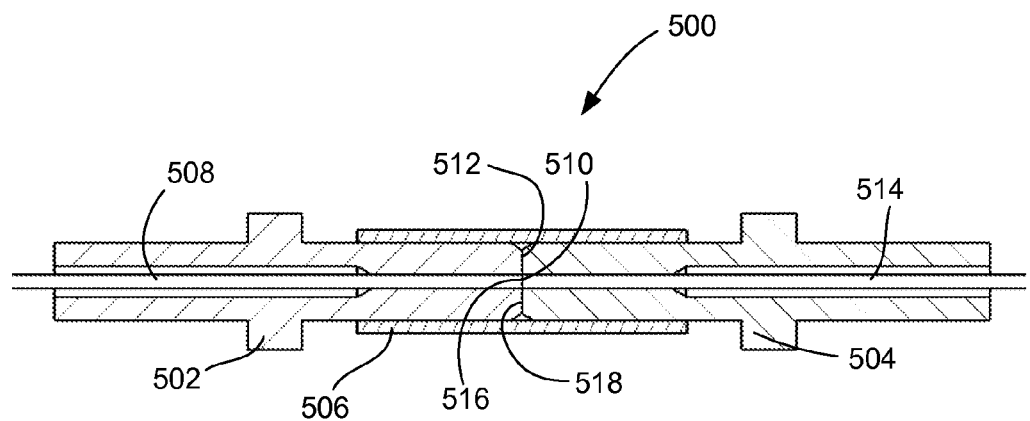
FIG. 29 is a diagrammatic, partially cut-away illustration, in elevation, of components of an embodiment of a connector which can be used for simultaneously transferring imaging and illumination light.

Referring now to FIG. 29, an embodiment of an optical connector 500 is shown for simultaneously transferring illumination and imaging light between a working assembly and an imaging assembly of an endoscope. The connector shown in FIG. 29 is simplified for illustrative purposes and is suitable for integration into the endoscope shown in FIG. 28. Connector 500 includes a working assembly ferrule 502 and an imaging assembly ferrule 504 along with a connector mating sleeve 506 for axially aligning the working assembly and imaging assembly ferrules. The working assembly ferrule is attached to a working assembly fiber segment 508 that has a proximal end face 510 which is polished and is coplanar with a working assembly ferrule end face 512. The imaging assembly ferrule supports an imaging assembly rod GRIN lens 514 that has a distal end face 516 that is coplanar with an imaging assembly ferrule end face 518 and a proximal end face 520 that can be positioned for receiving illumination light from a light source and for transferring image light to a viewing device, such as a camera system or eyepiece. The GRIN lens can include multiples of a single pitch (for instance a pitch 4 SRL) that propagate the image through a series of foci until, in the case of a lens with an integer pitch, it is displayed on the proximal end of the rod lens.

Figure 30:
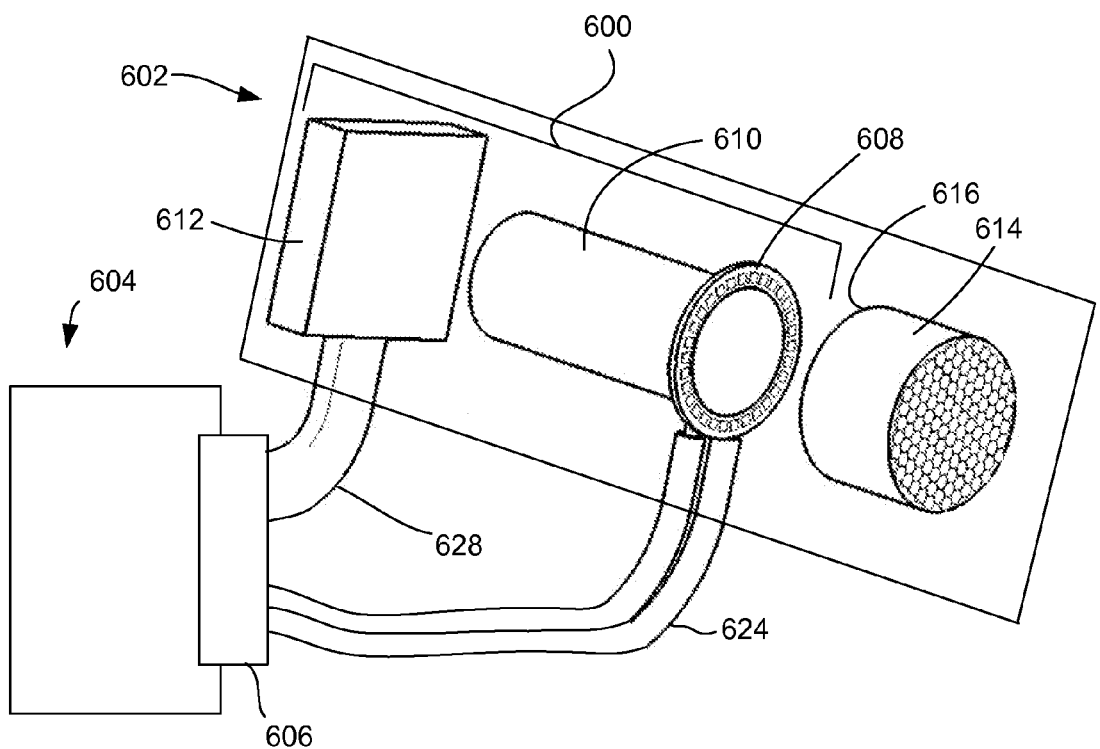
FIG. 30 is a diagrammatic view, partially in perspective, shown here to illustrate components of an embodiment of an endoscope which utilizes a single coherent fiber bundle for simultaneously transferring illumination and imaging light.
Figure 31:
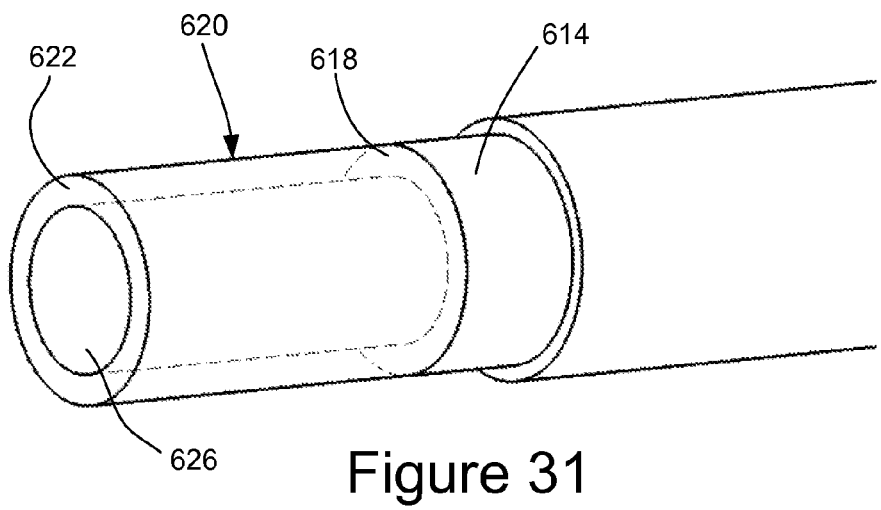
FIG. 31 is a diagrammatic illustration, in perspective, of an embodiment of a distal end of a working assembly of the endoscope of FIG. 30, shown here to illustrate further details with respect to its structure.

Referring now to FIGS. 30 and 31, an endoscopic imaging and illumination arrangement 600 is shown which can be utilized in an endoscope device for simultaneously illuminating and imaging through a single coherent fiber bundle arrangement. In one embodiment, endoscope arrangement 600 can be incorporated into a working assembly 602 and can be selectively coupled to an imaging assembly 604 using a connector 606. Endoscope arrangement 600 includes a micro LED ring light source 608, a GRIN imaging lens 610 and an electronic image detector 612 which can be a CCD array, for instance. The working assembly includes a coherent fiber bundle 614 having a proximal end 616 and a distal end 618 (FIG. 31) which is arranged for insertion into a viewing area.

The micro LED ring can be electrically interfaced to connector 606 by a cable 624 to receive power. The micro LED ring can contain micro LEDs that are arranged around a printed circuit board to produce an annularly-shaped illumination light. The micro LED ring can include integrated focusing optics which provide a high coupling efficiency of around 60% to 80% of the illumination light from the LEDs into an annular area at the proximal end of the coherent fiber bundle. Because of the high efficiency of the coupling, the micro LED ring can consume less power than light sources with lower coupling efficiencies. Lower power consumption can result in low operating temperatures and longer LED life. The light source is shown in a spaced apart relationship from the proximal end of the coherent fiber bundle for clarity, because the outer diameter of the micro LED ring is similar in size to the outer diameter of the coherent fiber bundle. In actual practice, the micro LED ring can be placed directly against the fiber bundle. The LEDs of the micro LED ring can produce narrowband illumination such as, for example, blue illumination. Therefore, the distal end of the coherent fiber bundle can include a light guide cylinder 620 (FIG. 31) which can receive the illumination light from the annular fibers at the circumference of the bundle and emit the light into the viewing area through a distal end face 622. Light guide cylinder 620 can include a fluorescing phosphor material to convert the narrowband illumination into white light. Conversion to white light at the distal end of the fiber bundle produces a wide field of the illumination without the use of additional optics.

The distal end of the coherent fiber bundle (FIG. 31) can also include a GRIN objective lens 626 for imaging the viewing area and transferring image light to the ends of fibers in a center area at the distal end of the fiber bundle, which then carry the image light to a circular area at the proximal end of the fiber bundle inside of the annular ring of fibers that receive the light from the micro LED light source. GRIN imaging lens 610 (FIG. 30) images the proximal end of the fiber bundle while receiving the image light for transfer to electronic image detector 612.

The image detector can be a CCD array and can include multiple individual pixel sensors for each of the fiber cores in the fiber bundle. Stated in another way, the CCD array can include a higher pixel resolution than a pixel resolution that would be represented by the area density of the fiber cores. Image detector 612 can be electrically connected to connector 606 using a cable 628 which can be used to provide power to the image detector and to carry data signals between the image detector and the connector. Separate electrical connectors can be provided for the micro LED light source and the electronic image detector or all connections can be integrated into one electrical connector as shown.

In one embodiment, imaging assembly 604 can be integrated with the working assembly. The imaging assembly can receive imaging data from the electronic image detector and can convert that data into an image that can be viewed. In another embodiment, power can be provided by a power source integrated into the working assembly. In another embodiment, the electronic image detector can be replaced by one or more lenses, such as would be found in an eyepiece. In yet another embodiment, endoscope arrangement 600 can be integrated into an imaging assembly and an optical arrangement can transfer the image and illumination light between the imaging assembly and the working assembly.

Figure 32:
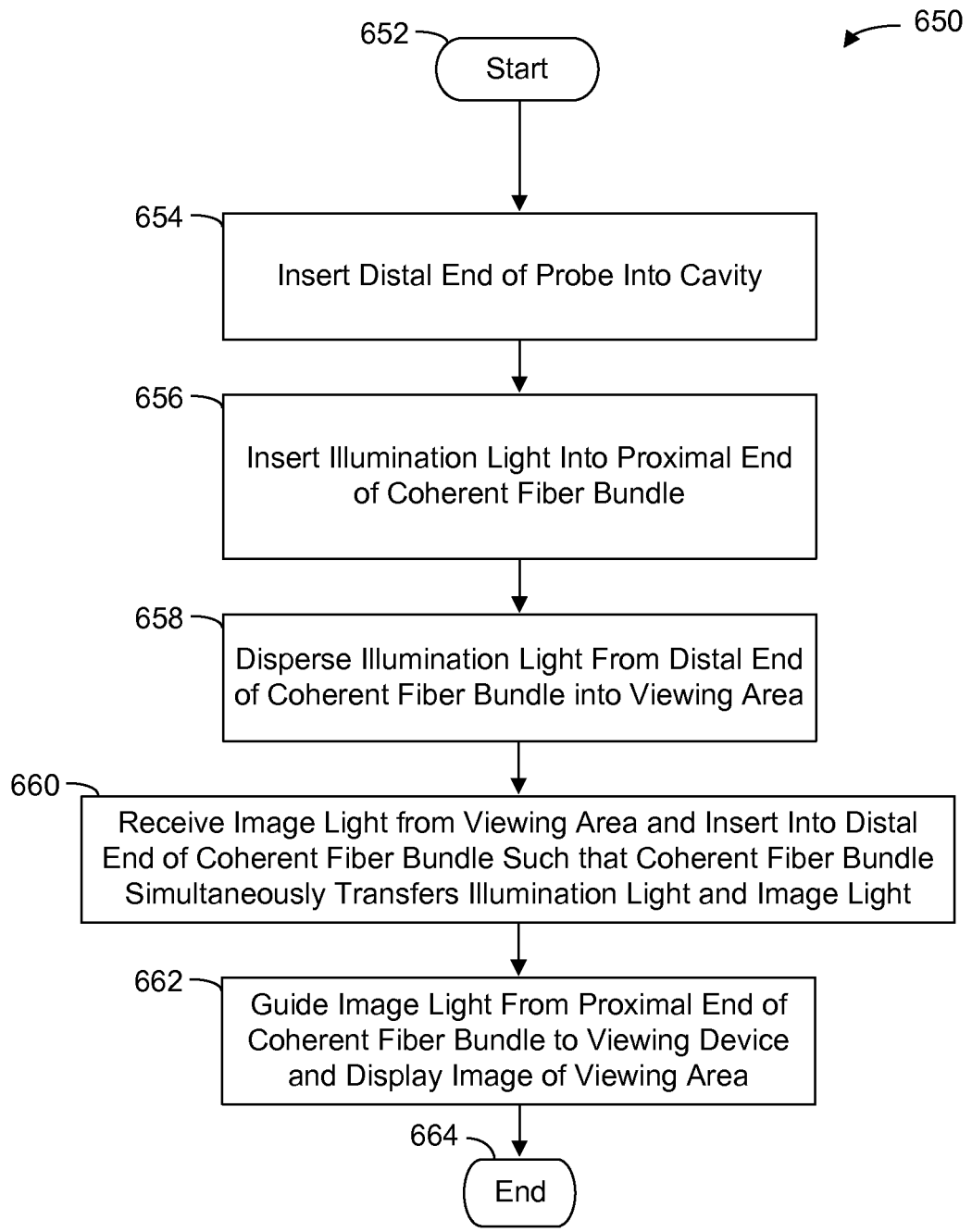
FIG. 32 is a method diagram for endoscopically imaging a viewing area in a cavity.

Referring now to FIG. 32, a method 650 is shown for endoscopically imaging a viewing area into a cavity. A method 650 begins at 652 and proceeds to 654 where a distal end of an endoscopic probe is inserted into a cavity. The endoscopic probe includes a coherent fiber bundle having a plurality of different fibers that are surrounded by a common cladding. The coherent fiber bundle is configured to transfer light between a distal end and a proximal end through the fibers and the coherent fiber bundle is arranged with the distal end of the coherent fiber bundle at the distal end of the probe. The method 650 then proceeds to 656 where illumination light is inserted into the proximal end of the coherent fiber bundle which transfers the illumination light from the proximal end of the coherent fiber bundle to the distal end of the coherent fiber bundle. Method 650 then proceeds to 658 where the illumination light is dispersed from the distal end of the coherent fiber bundle into the viewing area of the cavity. Method 650 then proceeds to 660 where image light is received from the viewing area and inserted into the distal end of the coherent fiber bundle which transfers the image light from the distal end to the proximal end. The image light includes illumination light reflected from the viewing area. The coherent fiber bundle simultaneously transferring the illumination light and the image light. Method 650 then proceeds to 662 where the image light is guided from the proximal end of the coherent fiber bundle to a viewing device. The image light and viewing device are used to display an image of the viewing area. Method 650 then proceeds to 664 where the method ends.

Many advantages can be gained by the various embodiments described herein. The co-propagation of the illumination and the image in the same imaging fiber bundle decreases the number of endoscope components which reduces the cost of the endoscope. Moreover, the manner of construction allows the glass cylinder and GRIN lens assembly to be passively placed. Employing a single imaging fiber bundle arrangement enables t feasibility with respect to employing a common fiber optic SC/PC connector as an interface between the expensive optics/illumination imaging assembly and the disposable endoscope working assembly (tip). Decreasing the cost of the working assembly and producing the working assembly as a separate component from the imaging assembly allows the working assembly to be disposable to enhance economic feasibility. A properly constructed optics/illumination imaging assembly can have internal optics that allows the use of a variety of sizes of imaging fibers on the disposable endoscope working assembly. Incorporating the fiber ferrule into a common medical y-tube allows for the construction of an economical endoscope working assembly with a built-in working channel.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:
1. An endoscope, comprising:
an elongated coherent fiber bundle including a distal end and a proximal end having an end face that is circular, wherein the coherent fiber bundle includes a plurality of different fibers that are surrounded by a common cladding and the coherent fiber bundle is configured to transfer light between the distal and proximal ends through the fibers;
a working assembly including an elongated probe having a distal end for insertion into a viewing area and a proximal end for manipulating the distal end of the probe, and wherein the distal end of the elongated coherent fiber bundle is positioned at the distal end of the probe;

an imaging assembly including a viewing device for receiving and modifying image light for viewing, and wherein the end face of the proximal end of the coherent fiber bundle is positioned at the imaging assembly and the imaging assembly is configured to transfer image light from the end face of the proximal end of the coherent fiber bundle to the viewing device;

an illumination light source, forming part of the imaging assembly, for generating illumination light and inserting the illumination light into an annular shaped area of said end face corresponding to a first portion of the fibers at the proximal end of the coherent fiber bundle which transfers the illumination light to the distal end of the coherent fiber bundle, the illumination light source arranged such that the illumination light is inserted into the annular shaped area of said end face of the proximal end of the coherent fiber bundle at least essentially without the illumination light interacting with the image light between the proximal end of the coherent fiber bundle and the viewing device and the imaging assembly is configured to receive image light from a circular area corresponding to a second, different portion of the fibers inside the annularly shaped area and to transfer the image light to the viewing device, the illumination source including illumination light generating elements that are annularly arranged around an aperture for illuminating the annular shaped region on said end face and an illumination lens that is arranged to receive the illumination light and to focus the illumination light into said annular shaped area on the end face of the proximal end of the coherent fiber bundle;

an imaging lens in the imaging assembly that images the circular area within the annular area on the proximal end of the coherent fiber bundle to collect image light from the circular area for transfer to the viewing device;

a lens arrangement forming part of the working assembly and positioned at the distal end of the elongated probe, the lens arrangement including an illumination portion arranged to receive the illumination light from the first portion of fibers at the distal end of the coherent fiber bundle and to disperse the illumination light into the viewing area, the lens arrangement also including an imaging portion that is different than the illumination portion and that is arranged to receive image light from the viewing area including illumination light reflected from the viewing area and to insert the image light into the second portion of fibers at the distal end of the coherent fiber bundle for transfer to the circular area at the proximal end of the coherent fiber bundle where the image light is then transferred to the imaging assembly; and a mechanical stage, forming part of the imaging assembly, that supports the illumination lens and the imaging lens for selective movement to resize the annular shaped area and to resize the circular area to accommodate different sizes of coherent fiber bundles.

2. The endoscope as defined in claim 1, wherein the end face is at least generally planar.

3. The endoscope as defined in claim 1, wherein the imaging portion of the lens arrangement includes a GRIN lens that is configured to transfer image light from the viewing area into the distal end of the fibers corresponding to the circular area of the fibers at the proximal end of the coherent fiber bundle.

4. The endoscope as defined in claim 3, wherein the illumination portion of the lens arrangement includes a working assembly light guide hollow cylinder that is configured with a proximal end face to receive illumination light from the first portion of the fibers surrounding the second portion of the fibers at the distal end of the coherent fiber bundle and to carry the illumination light to a distal end face of the light guide hollow cylinder for emission therefrom to illuminate the viewing area.

5. The endoscope as defined in claim 4, wherein the working assembly light guide hollow cylinder is positioned at least partially around the GRIN lens.

6. The endoscope as defined in claim 5, wherein the GRIN lens includes an outside diameter that is sufficiently smaller than an inside diameter of the light guide hollow cylinder such that the GRIN lens interference fits inside of the cylindrical light guide.

7. The endoscope as defined in claim 1, wherein the illumination portion of the lens arrangement includes a working assembly light guide hollow cylinder that is configured with an annular proximal end face to receive illumination light from the first portion of the fibers at the distal end of the coherent fiber bundle and to carry the illumination light to an annular distal end face of the hollow cylinder from which the illumination light is emitted into the viewing area.

8. The endoscope as defined in claim 7, wherein the annular distal end face of the cylinder is frosted to scatter the illumination light into the viewing area.

9. The endoscope as defined in claim 7, wherein the annular distal end face of the hollow cylinder includes a rounded configuration to disperse the illumination light into the viewing area.

10. The endoscope as defined in claim 7, wherein the annular distal end face of the cylinder includes a polished finish to concentrate the illumination light at a specific distance from the cylinder end face.

11. The endoscope as defined in claim 10, wherein the annular distal end face of the cylinder is polished based at least in part on a specific wavelength of the illumination light for emitting the specific wavelength.

12. The endoscope as defined in claim 1, wherein the mechanical stage is electrically controlled.

13. The endoscope as defined in claim 1, further comprising:

an optical connector that is arranged to selectively optically couple the working assembly and the imaging assembly for simultaneously transferring the imaging light and the illumination light, the optical connector including a working assembly connector portion forming part of the working assembly and an imaging assembly connector portion forming part of the imaging assembly, and the working assembly connector portion including a working assembly ferrule and the imaging assembly connector portion including an imaging assembly ferrule, and wherein the coherent fiber bundle includes a working assembly segment forming part of the working assembly and an imaging assembly segment forming part of the imaging assembly, the imaging assembly segment configured with a higher density of fibers than the working assembly segment, the working assembly segment having a proximal end that is attached to the working assembly ferrule and the imaging assembly segment having a distal end that is attached to the imaging assembly ferrule, the optical connector including a connector mating sleeve for axially aligning the working assembly ferrule and the imaging assembly ferrule to axially align the proximal end of the working assembly segment to the distal end of the imaging assembly segment when the optical connector connects the working assembly to the imaging assembly such that each fiber of the working assembly segment optically couples to multiple fibers of the imaging assembly segment of the coherent fiber bundle.

14. The endoscope as defined in claim 13, wherein the optical connector includes a GRIN lens to transfer light between the working assembly connector portion and the imaging assembly connector portion.

15. The endoscope as defined in claim 1, further comprising:
an optical connector that is arranged to selectively optically connect the working assembly and the imaging assembly for simultaneously transferring the imaging light and the illumination light, the optical connector including a working assembly connector portion forming part of the working assembly and an imaging assembly connector portion forming part of the imaging assembly, the working assembly connector portion including a working assembly ferrule and the imaging assembly connector portion including an imaging assembly ferrule, the imaging assembly including a rod GRIN lens having a proximal end face and a distal end face and which is configured to couple light between the proximal end face and the distal end face, and wherein the proximal end of the coherent fiber bundle is attached to the working assembly ferrule and the distal end of the rod GRIN lens is attached to the imaging assembly ferrule, the optical connector including a connector mating sleeve for axially aligning the working assembly ferrule and imaging assembly ferrule to axial align the proximal end of the coherent fiber bundle to the distal end of the rod GRIN lens when the optical connector connects the working assembly to the imaging assembly.

* * * * *